(12) United States Patent
Kushibiki et al.

(10) Patent No.: US 6,376,695 B1
(45) Date of Patent: Apr. 23, 2002

(54) ORGANOSILICON-MODIFIED CHARGE TRANSPORTING COMPOUND AND CURABLE COMPOSITION CONTAINING THE COMPOUND AND HAVING CHARGE TRANSPORTING ABILITY

(75) Inventors: Nobuo Kushibiki, Fujisawa; Kikuko Takeuchi, Odawara; Hideki Kobayashi; Toru Masatomi, both of Ichihara; Kazuo Yoshinaga, Kawasaki; Yuichi Hashimoto, Tokyo; Shunichiro Nishida, Yokohama, all of (JP)

(73) Assignees: Dow Corning Asia Ltd.; Dow Corning Toray Silicone Co., Ltd.; Canon Kabushiki Kaisha, all of Tokyo (JP)

( * ) Notice: Subject to any disclaimer, the term of this patent is extended or adjusted under 35 U.S.C. 154(b) by 0 days.

(21) Appl. No.: 08/744,192

(22) Filed: Nov. 5, 1996

(30) Foreign Application Priority Data

Nov. 6, 1995 (JP) .............................. 7-287692

(51) Int. Cl.$^7$ .................................. C07F 7/10
(52) U.S. Cl. .......................... 556/413; 528/17; 528/33; 528/38
(58) Field of Search ............. 556/413; 528/17, 528/33, 38

(56) References Cited

U.S. PATENT DOCUMENTS

| | | | |
|---|---|---|---|
| 5,230,976 A | 7/1993 | Schank et al. | 430/59 |
| 5,232,801 A | 8/1993 | Rule et al. | 430/59 |
| 5,290,963 A * | 3/1994 | Mishima et al. | 556/413 |
| 5,326,661 A | 7/1994 | Sansone et al. | 430/20 |
| 5,352,554 A * | 10/1994 | Mishima et al. | 430/59 |
| 5,436,099 A | 7/1995 | Schank et al. | 430/59 |
| 5,688,961 A * | 11/1997 | Kushibiki et al. | 548/955 |
| 5,712,360 A * | 1/1998 | Kobayashi et al. | 528/38 |

FOREIGN PATENT DOCUMENTS

| | | |
|---|---|---|
| EP | 224784 | 11/1986 |
| EP | 446895 | 9/1991 |
| EP | 457212 | 11/1991 |
| JP | 55-95953 | 7/1980 |

* cited by examiner

*Primary Examiner*—Paul F. Shaver
(74) *Attorney, Agent, or Firm*—Fitzpatrick, Cella, Harper & Scinto

(57) ABSTRACT

An organosilicon-modified charge transporting compound having a structure represented by the following Formula (I):

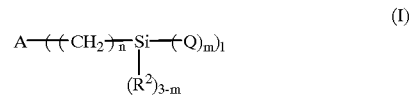

wherein A represents a charge transporting group, Q represents a hydrolytic group or a hydroxyl group, $R^2$ represents a monovalent hydrocarbon group or a halogen-substituted monovalent hydrocarbon group having 1 to 15 carbon atoms, n is 1 to 18, m is 1 to 3, and 1 is 1 to 5; and a curable composition containing the organosilicon-modified charge transporting compound and a cure type resin chiefly composed of an organosilicon high polymer.

10 Claims, 3 Drawing Sheets

ORGANOSILICON-MODIFIED CHARGE TRANSPORTING COMPOUND AND CURABLE COMPOSITION CONTAINING THE COMPOUND AND HAVING CHARGE TRANSPORTING ABILITY

BACKGROUND OF THE INVENTION

1. Field of the Invention

This invention relates to a charge transporting compound, and a curable composition containing the compound and having a charge transporting ability. More particularly, this invention relates to a charge transporting compound and a curable composition containing the compounds and having a charge transporting ability, which compound and composition have a superior durability such as wear resistance because of the high surface hardness, a good appearance because of the transparency, superior stain resistance and slip properties because of the small surface energy as well as the antistatic ability.

2. Related Background Art

Surfaces of plastics and soft metals such as aluminum tend to be scratched and soiled by mechanical and electrical action and, in an extreme case, become unserviceable because of wear. Stated specifically, plastic lenses, CRT surfaces, automobile bodies or the like may have problems in use as a result of damage caused by repeating abrasion or adhesion of rubber or the like.

In order to satisfy various properties and characteristics required for such surfaces, it has been attempted to provide various surface protective layers mainly composed of resin. For example, it is proposed to provide a surface protective layer to which metal oxide particles are added as conductive particles to control its wear resistance and electrical resistance.

It is also studied to add a variety of materials to improve the surface properties. For example, reports are made on additives taking note of the inherent small surface energy of silicone, such as silicone oil, polydimethylsiloxane, silicone resin powder, cross-linked silicone resin, poly(carbonate-silicon) block copolymer, silicone-modified polyurethane and silicone-modified polyester.

Fluorine type high polymers, such as polytetrafluoroethylene powder and carbon fluoride powder, have typically low surface energy.

Surface protective layers containing metal oxides or the like can be high in hardness, but may have problems in cleaning properties and so forth, because of the high surface energy. Silicone resins are advantageous in view of their small surface energy, but because of their low compatibility with other resins, they have problems such that they tend to agglomerate in the system to cause light scattering and that they may bleed to segregate at the surface, resulting in instability. The fluorine type high polymers, which are polymers of low surface energy, are commonly insoluble in solvents and also have a poor dispersibility. Hence, it is difficult to make smooth surfaces with them, and also because of their small refractive index light scattering tends to occur, causing the problem of transparency deterioration. Also, the fluorine type high polymers are commonly soft, and have the problem that the surface tends to be scratched. These resins have also the disadvantage that they are easily charged statically, because of their high electric resistance when used alone.

SUMMARY OF THE INVENTION

An object of the present invention is to provide an organosilicon-modified charge transporting compound and a curable composition containing the compound and having the charge transporting ability, that can solve the problems stated above, i.e., can form a surface layer having a charge transporting ability in a uniform state without bleeding or light scattering, a surface layer having a small surface energy and a mechanical and electrical durability at the same time.

First, the present invention is an organosilicon-modified charge transporting compound having a structure represented by the following Formula (I).

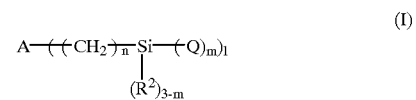

wherein A represents a charge transporting group, Q represents a hydrolytic group or a hydroxyl group, $R^2$ represents a monovalent hydrocarbon group or a halogen-substituted monovalent hydrocarbon group having 1 to 15 carbon atoms, n is 1 to 18, m is 1 to 3, and l is 1 to 5.

Second aspect of the present invention is a curable composition having a charge transporting ability, which comprises;

a cure type resin chiefly composed of an organosilicon high polymer in which monovalent hydrocarbon groups bonded to silicon atoms and the ratio of the silicon atoms and the hydrocarbon groups is from 0.5 to 1.5; and an organosilicon-modified charge transporting compound having a structure represented by the above Formula (I).

DESCRIPTION OF THE PREFERRED EMBODIMENTS

Figure 1:
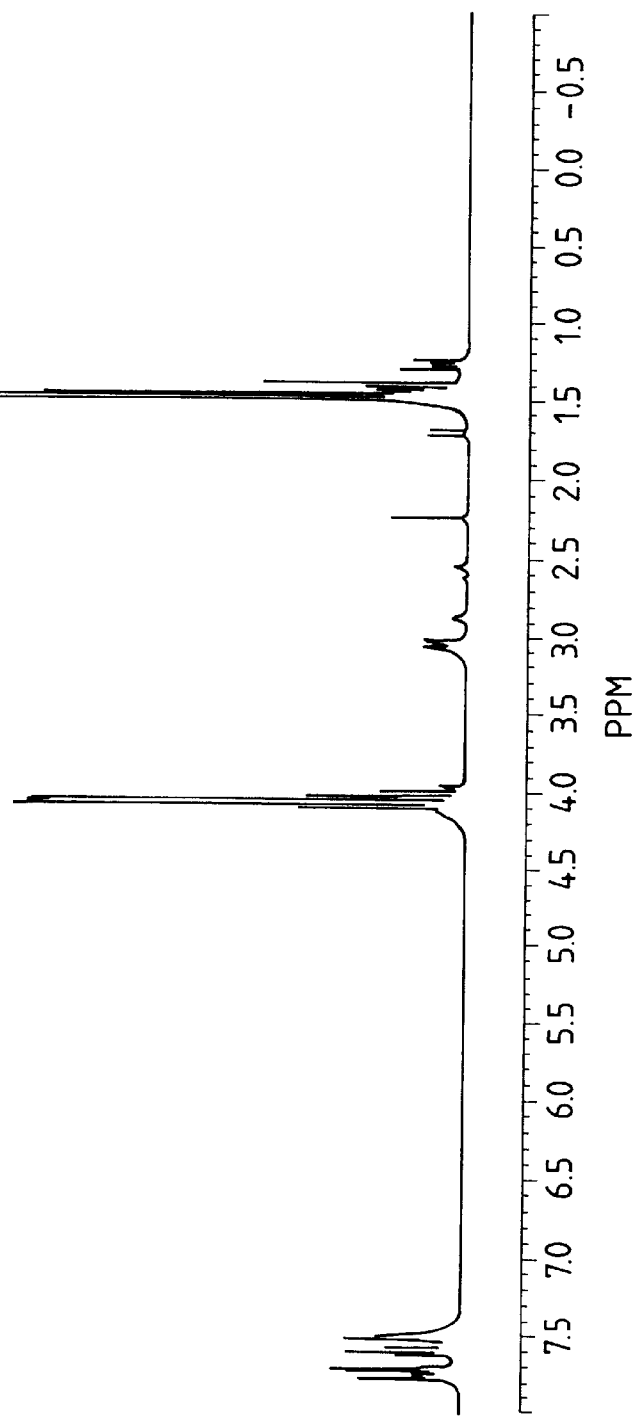
FIG. 1 shows an H-NMR spectrum of 4-[2-(triethoxysilyl)ethyl]triphenylamine in Example 1.

The organosilicon-modified charge transporting compound of the present invention has a structure represented by the following Formula (I).

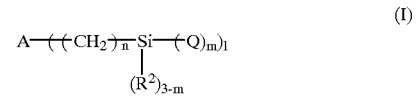

wherein A represents a charge transporting group, Q represents a hydrolytic group or a hydroxyl group, $R^2$ represents a monovalent hydrocarbon group or a halogen-substituted monovalent hydrocarbon group having 1 to 15 carbon atoms, n is 1 to 18, m is 1 to 3, and l is 1 to 5.

In the above Formula (I), the hydrolytic group represented by Q may include a methoxy group, an ethoxy group, a methylethyl ketoxime group, a diethylamino group, an acetoxy group, a propenoxy group, a propoxy group, a butoxy group and a methoxyethyl group, and more preferably a group represented by —$OR^1$, where $R^1$ represents a group that forms hydrolyzable alkoxyl group or alkoxyalkoxyl group, and is an alkyl or alkoxyalkyl group having 1 to 6 carbon atoms including a methyl group, an ethyl group, a propyl group, a butyl group, a pentyl group, a hexyl group and a methoxyethyl group. As Q, an alkoxyl group represented by the formula —$OR^1$ is preferred. In general, condensation of organosilicon compounds themselves may hardly take place when the number m of the hydrolytic groups bonded to the silicon atom is 1, so that polymerization reaction is suppressed. When, m is 2 or 3, the condensation reaction may readily take place with possible high cross-linking reaction. Hence, in spite of expected improvements in the hardness etc. of cured products, the obtained high polymer may cause changes in solubility in and reactivity with silicon type heat-curable resins.

$R^2$ is a group directly bonded to the silicon atom, representing a monovalent hydrocarbon group having 1 to 15 carbon atoms, including a methyl group, an ethyl group, a propyl group, a butyl group and a pentyl group. It may further include alkenyl groups such as a vinyl group and an allyl group, and aryl groups such as a phenyl group and a tolyl group. It may further include a halogen-substituted monovalent hydrocarbon group such as fluorohydrocarbon groups exemplified by trifluoropropyl group, a heptafluoropentyl group and a nonafluorohexyl group.

The letter symbol n is 1 to 18, and the alkylene group need not be a straight-chain. If n is 19 or more, the charge transporting group A may so readily move as to cause decrease in hardness. The charge transporting group directly bonded to the silicon atom, because of steric hindrance etc., affects adversely the stability and physical properties. Preferably, n is 2 to 8. The numeral 1 is 1 to 5. If 1 is 6 or more, unreacted groups may increase in the curing reaction, resulting in a lowering of electrical properties.

The charge transporting ability in the present invention means the ability to transport charges and preferably the ionization potential is 6.2 eV or below. That is, the organosilicon-modified charge transporting compound represented by Formula (I) and the hydrogenated compound of charge transporting group A may preferably have an ionization potential of 6.2 eV or below, and particularly preferably 4.5 to 6.2 eV. If the ionization potential is above 6.2 eV, charge injection becomes difficult, and the compound tends to be charged. If it is less than 4.5 eV, the compound may be easily oxidized to cause deterioration. The ionization potential is measured by atmospheric photoelectron analysis using, e.g., a surface analyzer AC-1, manufactured by Riken Keiki K.K.

The charge transporting group A in the above Formula (I) may include, when shown as a hydrogenated compound thereof (a charge transporting material), oxazole derivatives, oxathiazole derivatives, imidazole derivatives, triarylamine derivatives such as triphenylamine, 9-(p-diethylaminostyryl)anthracene, 1,1-bis-(4-dibenzylaminophenyl)propane, styrylanthracene, styrylpyrazoline, phenylhydrazones, α-phenylstilbene derivatives, thiazole derivatives, triazole derivatives, phenazine derivatives, acridine derivatives, benzofuran derivatives, benzimidazole derivatives, thiophene derivatives, and N-phenylcarbazole derivatives.

The charge transporting group A may preferably be a group represented by the following Formula (II).

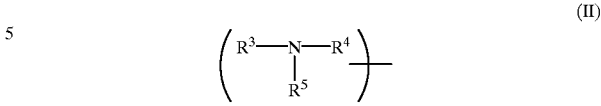

(II)

wherein $R^3$, $R^4$ and $R^5$ each represent an organic group, at least one of which represents an aromatic hydrocarbon ring group or a heterocyclic group, and $R^3$, $R^4$ and $R^5$ may be the same or different.

Thus, one hydrogen atom is removed from any one of the groups $R^3$, $R^4$ and $R^5$ to form the charge transporting group.

Preferred examples of structures represented by $R^3$, $R^4$ and $R^5$ are shown below.

In the following structural formulas, Ph indicates a phenyl group, Me a methyl group, Et an ethyl group, Bu a butyl group, and Pr a propyl group.

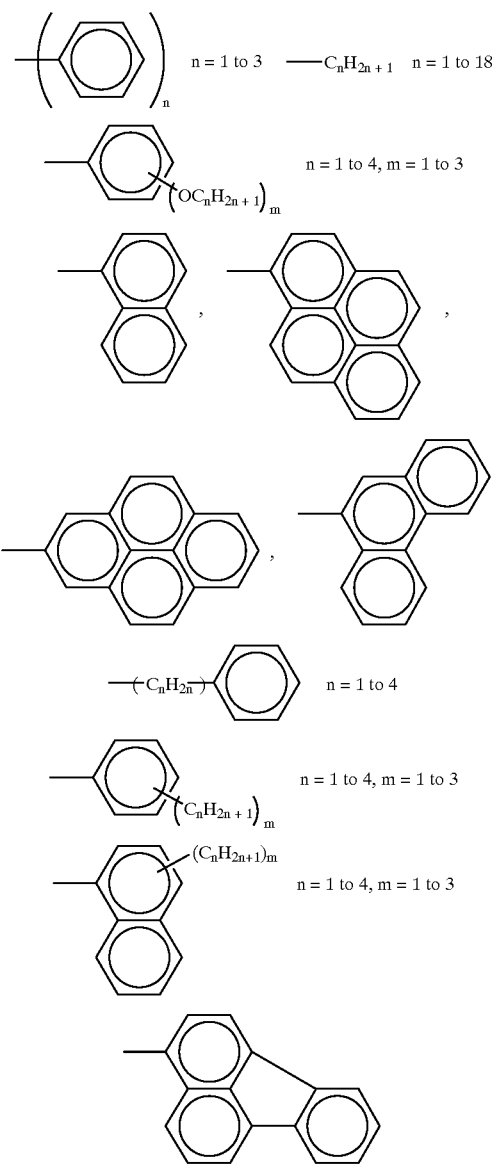

-continued
n = 1 to 4, m = 1 to 3
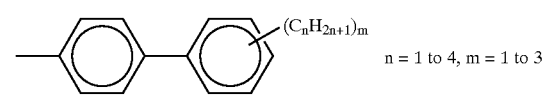
n = 1 to 4, m = 1 to 3
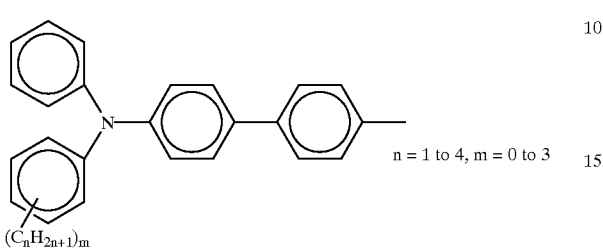
n = 1 to 4, m = 0 to 3
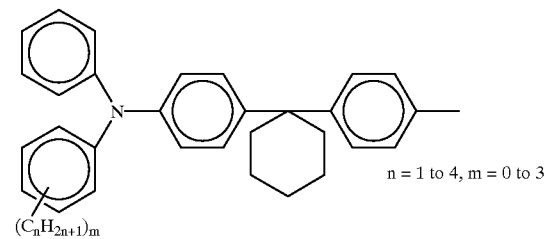
n = 1 to 4, m = 0 to 3
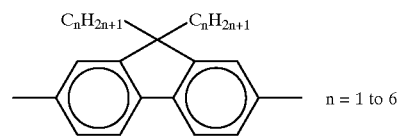
n = 1 to 6
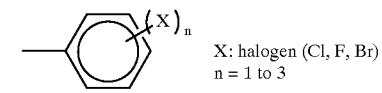
X: halogen (Cl, F, Br)
n = 1 to 3
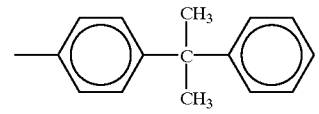
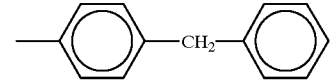
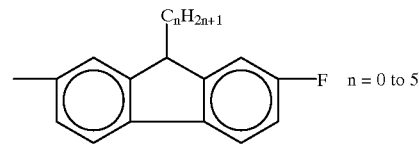
n = 0 to 5
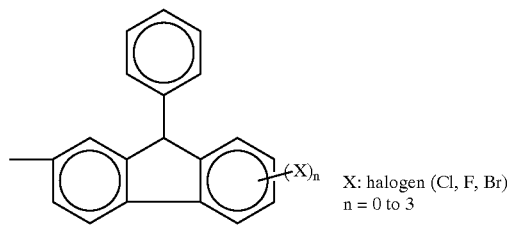
X: halogen (Cl, F, Br)
n = 0 to 3
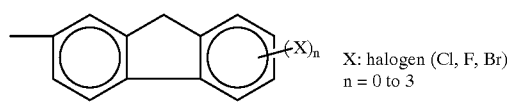
X: halogen (Cl, F, Br)
n = 0 to 3
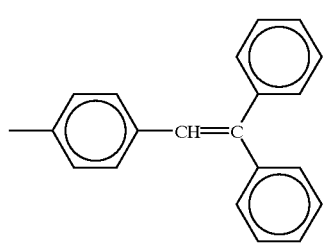
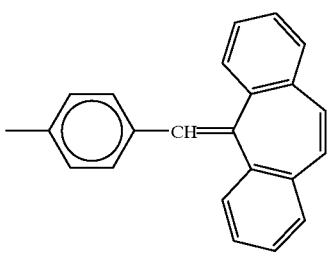
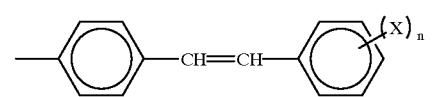
X: halogen (Cl, F, Br)
n = 0 to 3
Preferred examples of the hydrogenated compounds of the charge transporting group A are shown below.
Hydrazone type:
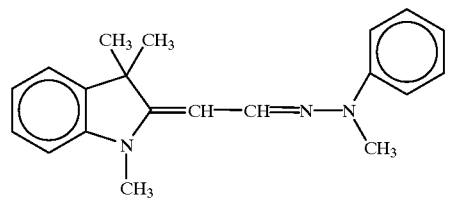
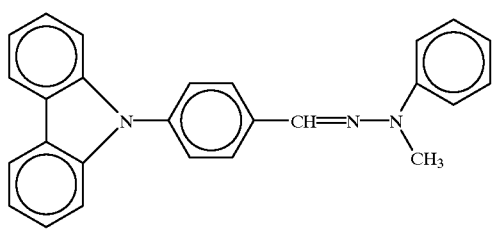
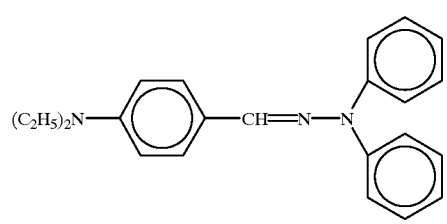
(oxidation potential: 0.57 V)
ionization potential: 5.22 eV

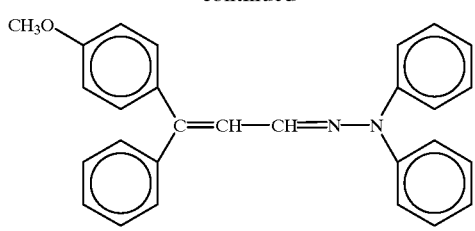
(oxidation potential: 0.84 V)
ionization potential: 5.47 eV
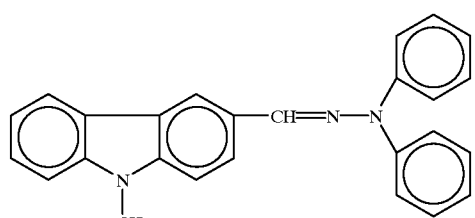
(oxidation potential: 0.83 V)
ionization potential: 5.47 eV
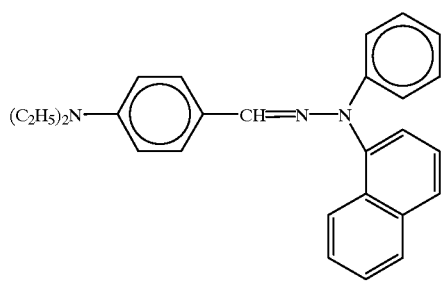
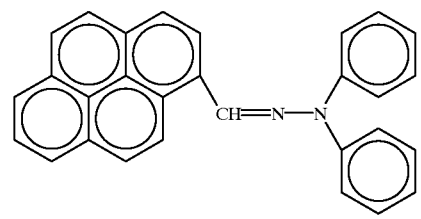
(oxidation potential: 0.91 V)
ionization potential: 5.54 eV
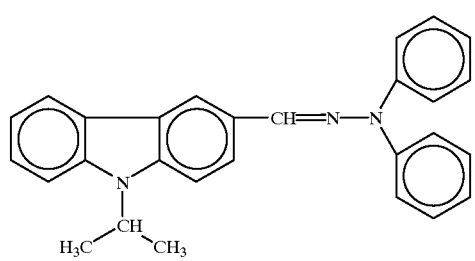
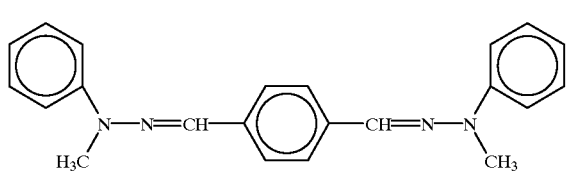
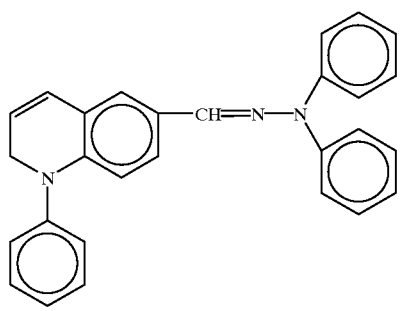
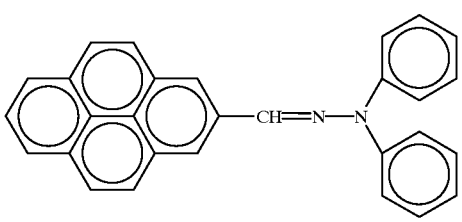
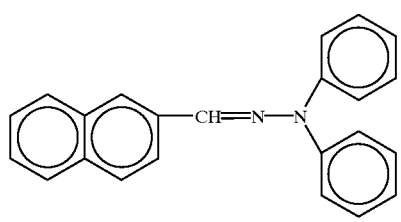
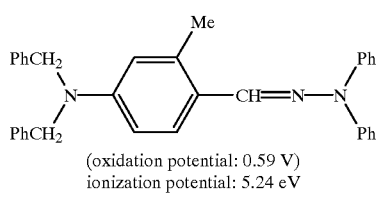
(oxidation potential: 0.59 V)
ionization potential: 5.24 eV
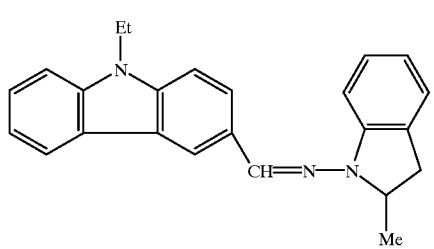
(oxidation potential: 0.65 V)
ionization potential: 5.30 eV
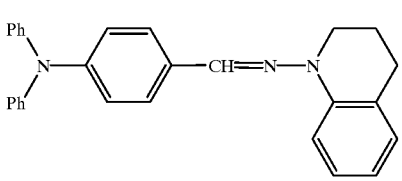
(oxidation potential: 0.65 V)
ionization potential: 5.30 eV -continued
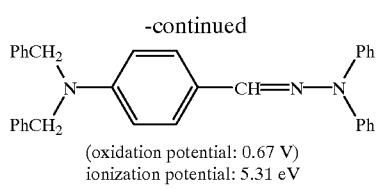
(oxidation potential: 0.67 V)
ionization potential: 5.31 eV
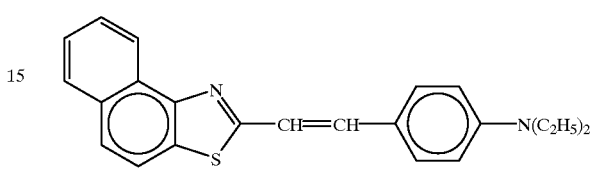
(oxidation potential: 0.76 V)
ionization potential: 5.40 eV
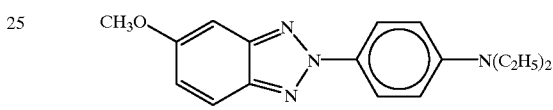
(oxidation potential: 0.81 V)
ionization potential: 5.47 eV
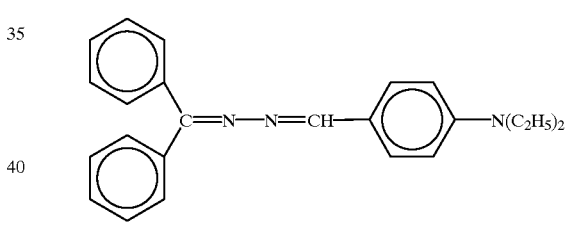
(oxidation potential: 0.83 V)
ionization potential: 5.47 eV
Pyrazoline type:
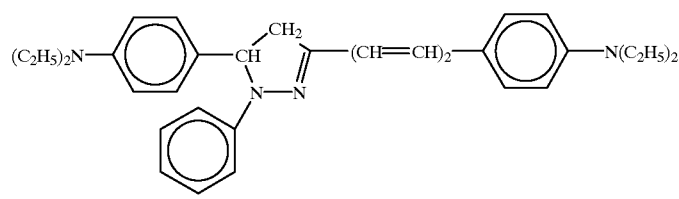
Oxazole type:
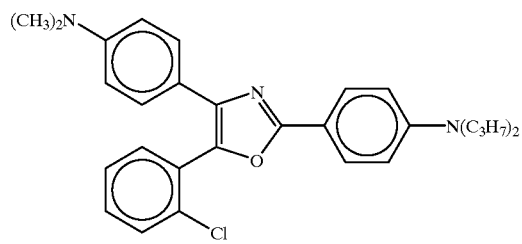
Oxadiazole type:
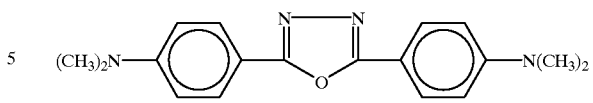
Thiazole type:
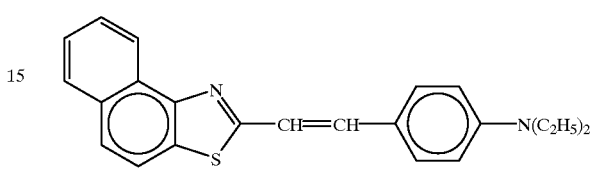
Triazole type:
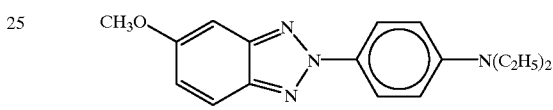
Azine type:
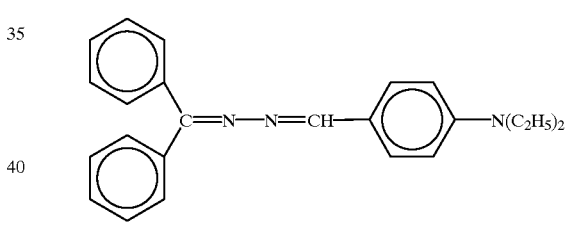
-continued
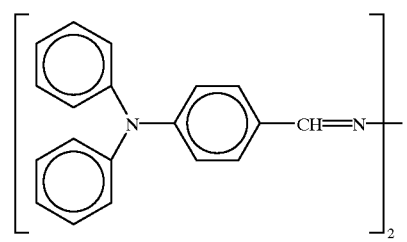

Dibenzylaniline type:
Triphenylamine type:
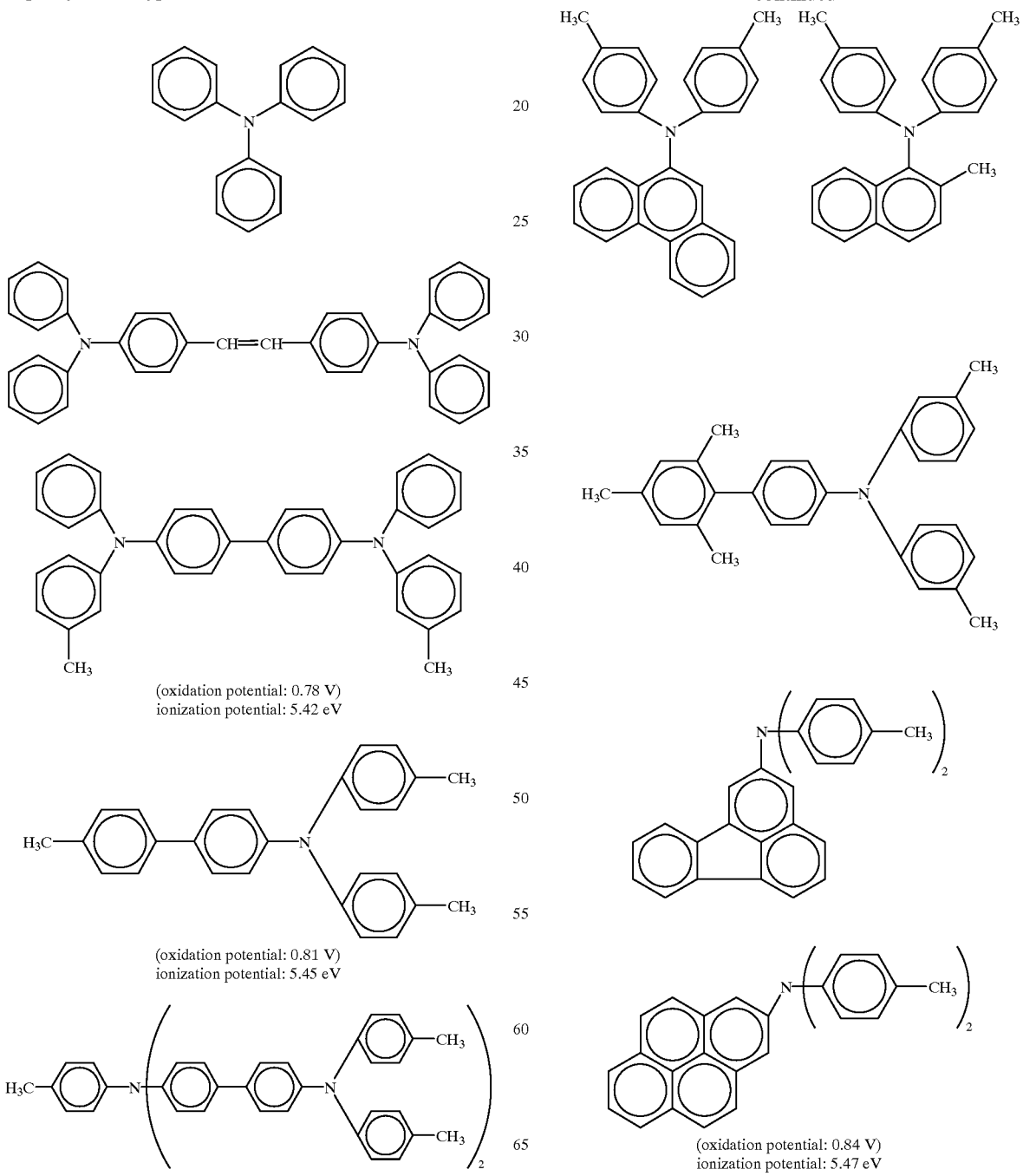
(oxidation potential: 0.78 V)
ionization potential: 5.42 eV
(oxidation potential: 0.81 V)
ionization potential: 5.45 eV
(oxidation potential: 0.84 V)
ionization potential: 5.47 eV -continued
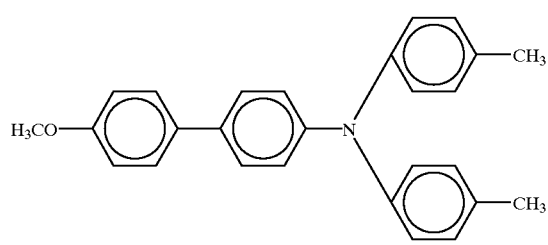
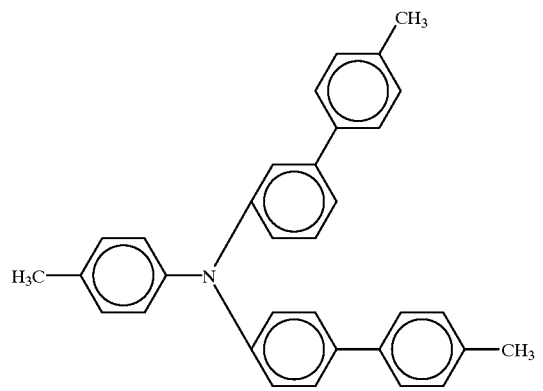
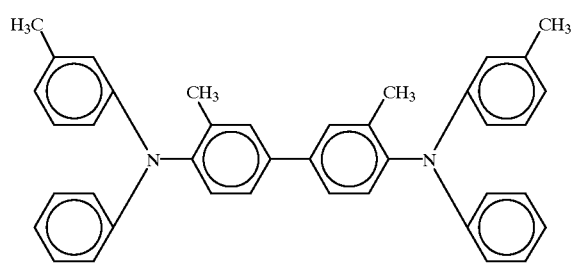
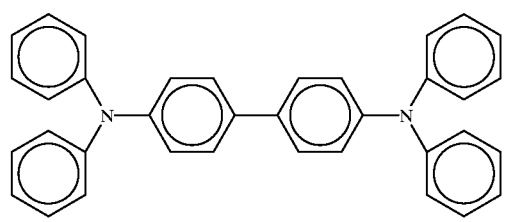
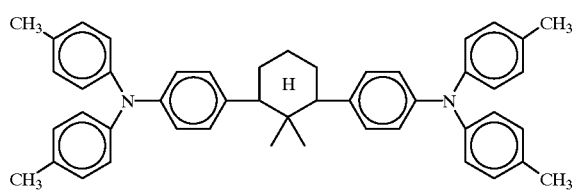
(oxidation potential 0.57 V)
ionization potential: 5.22 eV
-continued
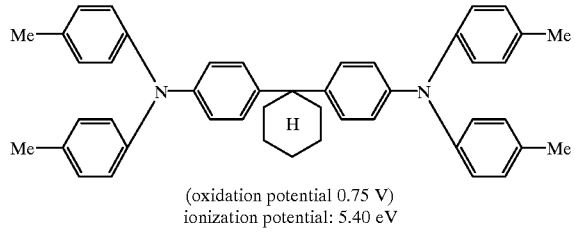
(oxidation potential 0.75 V)
ionization potential: 5.40 eV
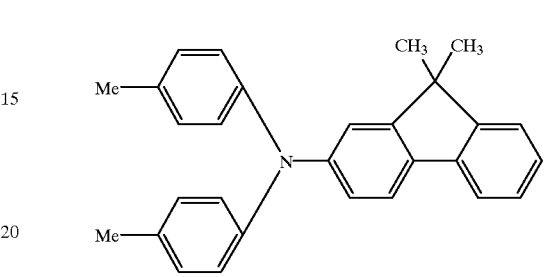
(oxidation potential 0.76 V)
ionization potential: 5.40 eV
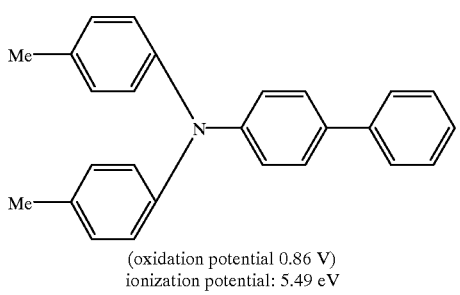
(oxidation potential 0.86 V)
ionization potential: 5.49 eV
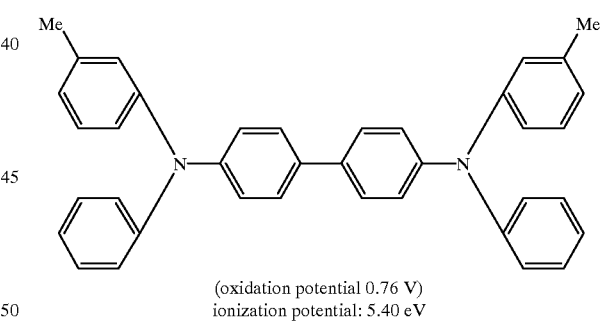
(oxidation potential 0.76 V)
ionization potential: 5.40 eV
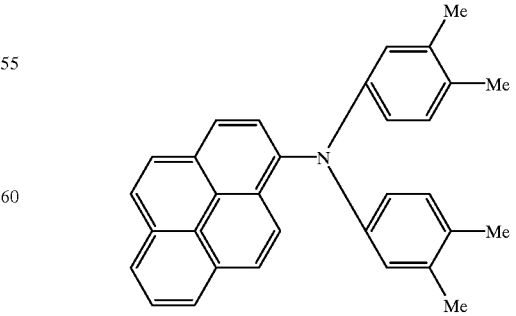
(oxidation potential 0.79 V)
ionization potential: 5.43 eV -continued

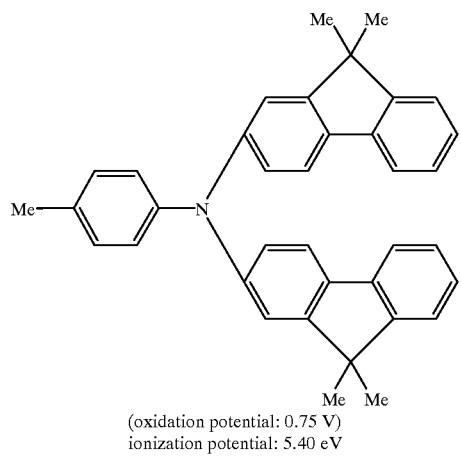
(oxidation potential: 0.75 V)
ionization potential: 5.40 eV

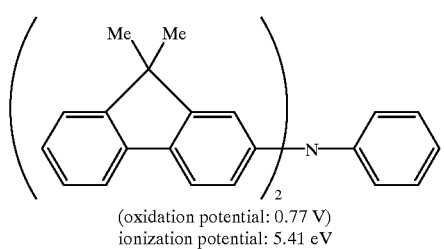
(oxidation potential: 0.77 V)
ionization potential: 5.41 eV

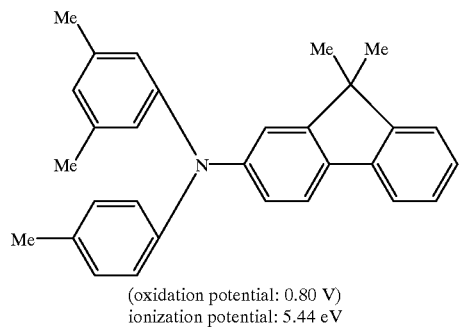
(oxidation potential: 0.80 V)
ionization potential: 5.44 eV

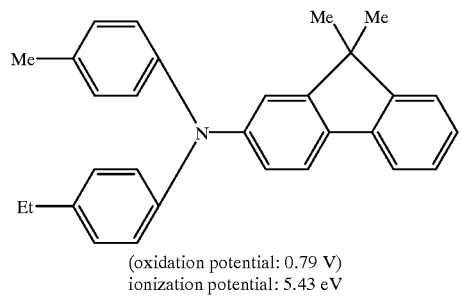
(oxidation potential: 0.79 V)
ionization potential: 5.43 eV

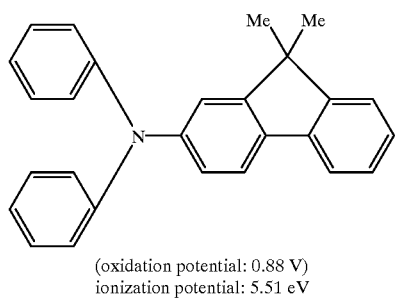
(oxidation potential: 0.88 V)
ionization potential: 5.51 eV

-continued

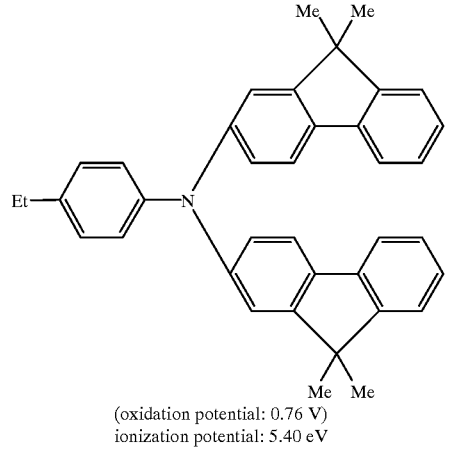
(oxidation potential: 0.76 V)
ionization potential: 5.40 eV

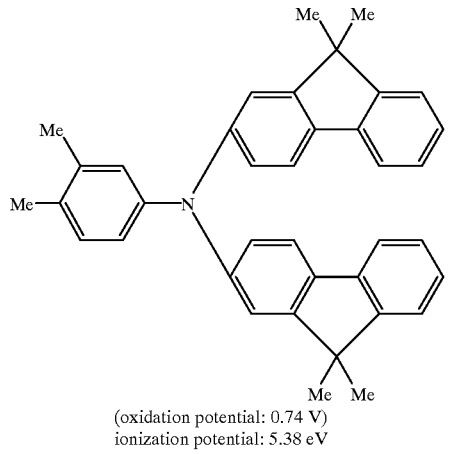
(oxidation potential: 0.74 V)
ionization potential: 5.38 eV

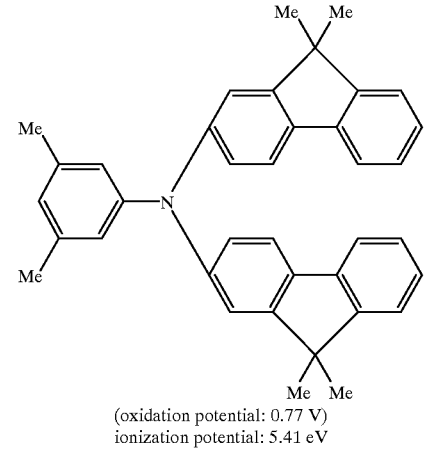
(oxidation potential: 0.77 V)
ionization potential: 5.41 eV

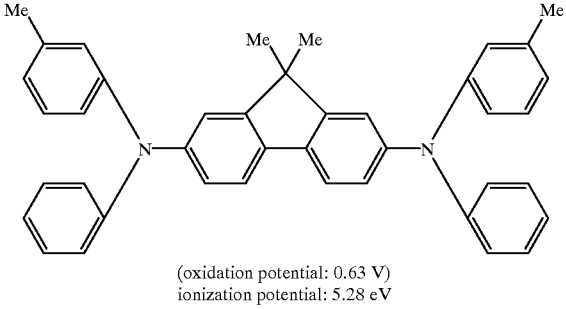
(oxidation potential: 0.63 V)
ionization potential: 5.28 eV

-continued

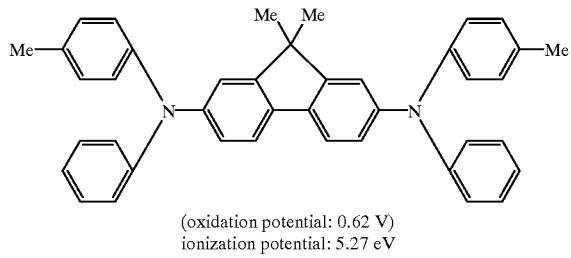
(oxidation potential: 0.62 V)
ionization potential: 5.27 eV

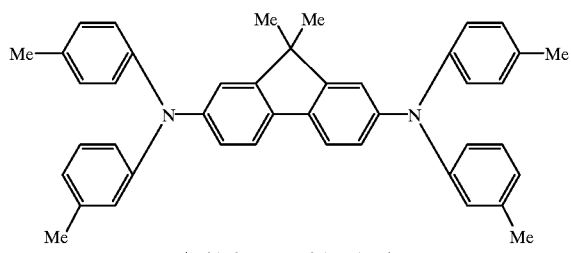
(oxidation potential: 0.58 V)
ionization potential: 5.22 eV

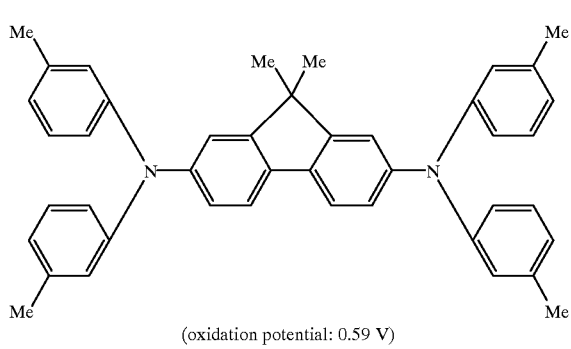
(oxidation potential: 0.59 V)
ionization potential: 5.23 eV

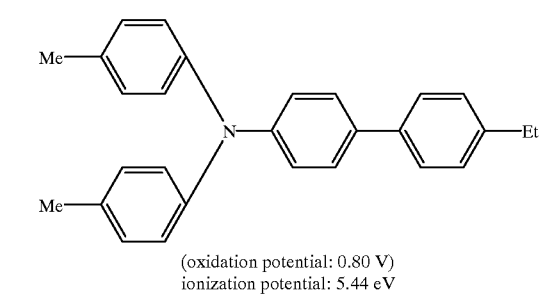
(oxidation potential: 0.80 V)
ionization potential: 5.44 eV

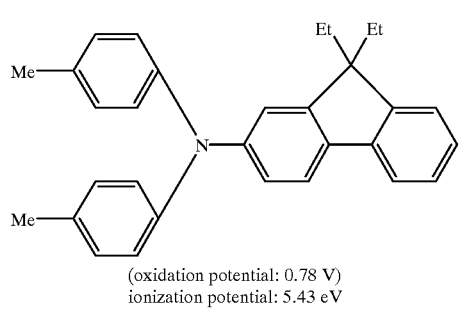
(oxidation potential: 0.78 V)
ionization potential: 5.43 eV

-continued

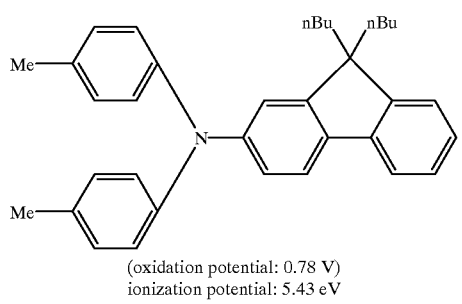
(oxidation potential: 0.78 V)
ionization potential: 5.43 eV

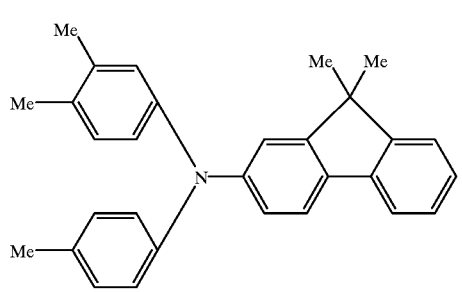
(oxidation potential: 0.76 V)
ionization potential: 5.41 eV

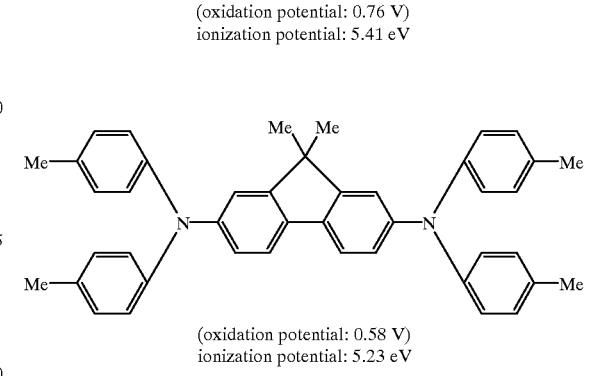
(oxidation potential: 0.58 V)
ionization potential: 5.23 eV

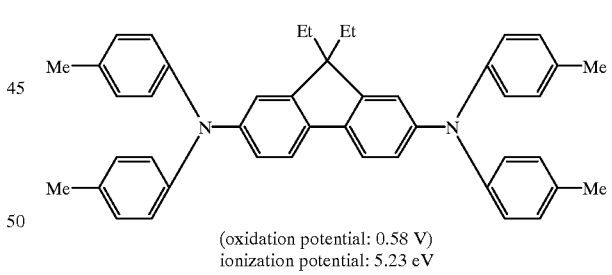
(oxidation potential: 0.58 V)
ionization potential: 5.23 eV

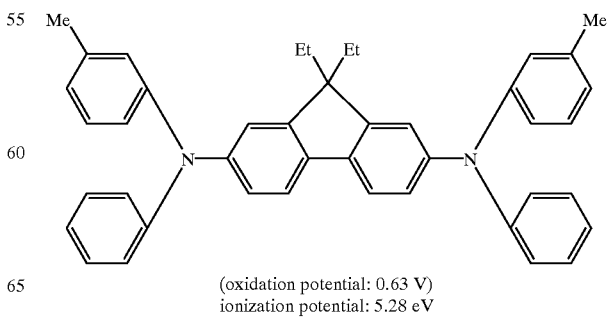
(oxidation potential: 0.63 V)
ionization potential: 5.28 eV

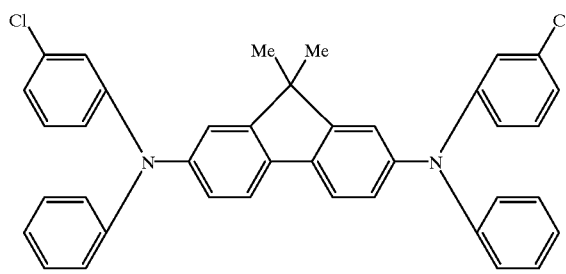

(oxidation potential: 0.77 V)
ionization potential: 5.41 eV

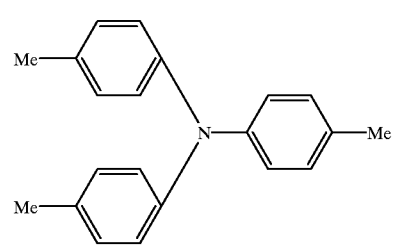

(oxidation potential: 0.83 V)
ionization potential: 5.47 eV

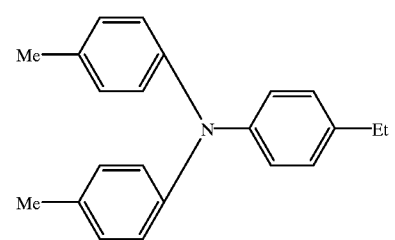

(oxidation potential: 0.83 V)
ionization potential: 5.47 eV

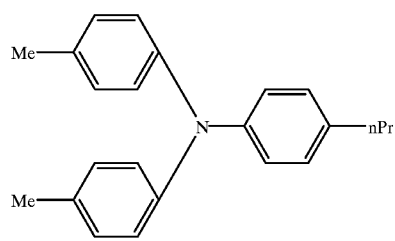

(oxidation potential: 0.84 V)
ionization potential: 5.47 eV

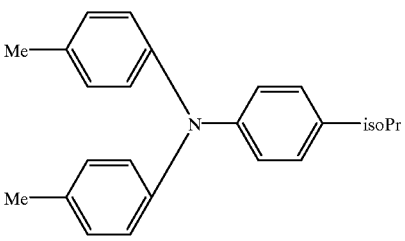

(oxidation potential: 0.83 V)
ionization potential: 5.47 eV

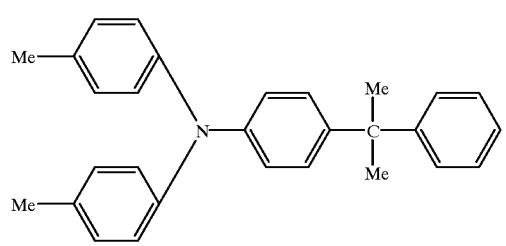

(oxidation potential: 0.83 V)
ionization potential: 5.47 eV

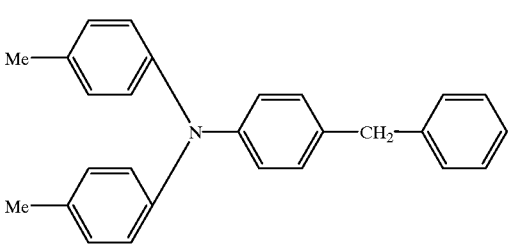

(oxidation potential: 0.85 V)
ionization potential: 5.48 eV

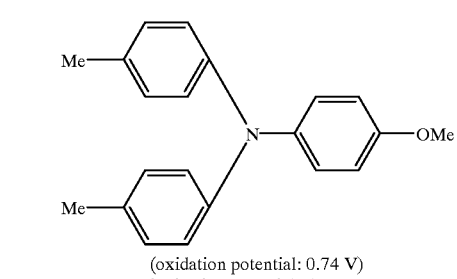

(oxidation potential: 0.74 V)
ionization potential: 5.38 eV

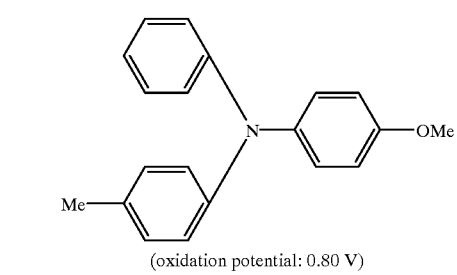

(oxidation potential: 0.80 V)
ionization potential: 5.44 eV

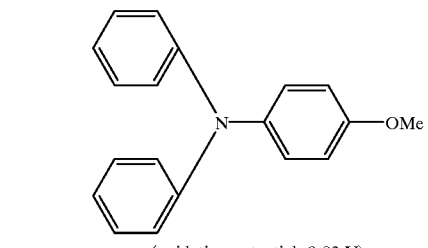

(oxidation potential: 0.83 V)
ionization potential: 5.47 eV

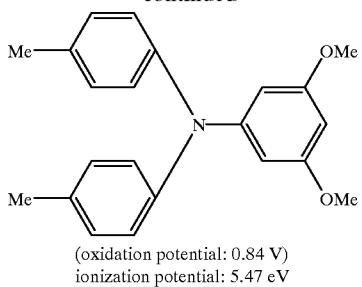
(oxidation potential: 0.84 V)
ionization potential: 5.47 eV
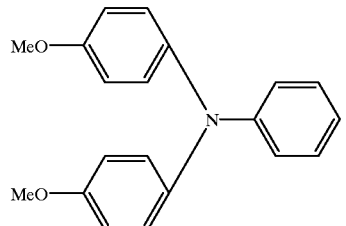
(oxidation potential: 0.72 V)
ionization potential: 5.36 eV
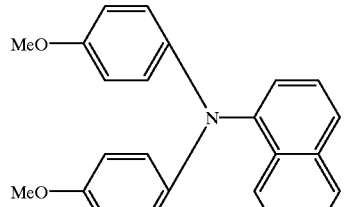
(oxidation potential: 0.73 V)
ionization potential: 5.38 eV
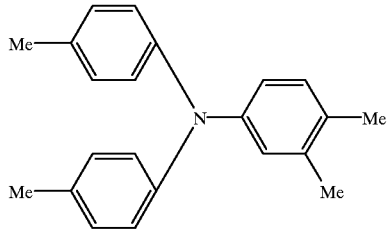
(oxidation potential: 0.81 V)
ionization potential: 5.45 eV
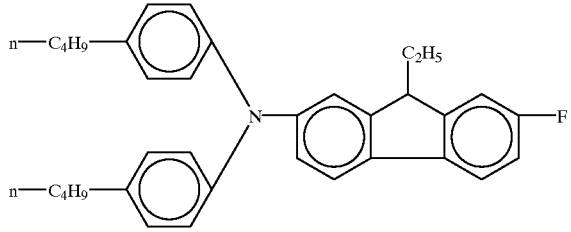
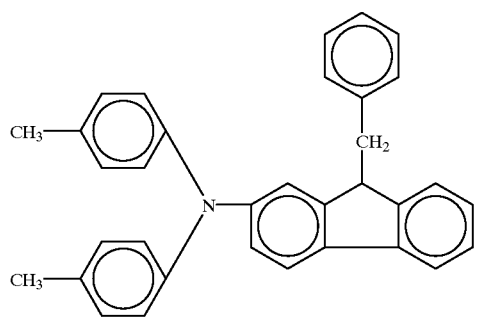
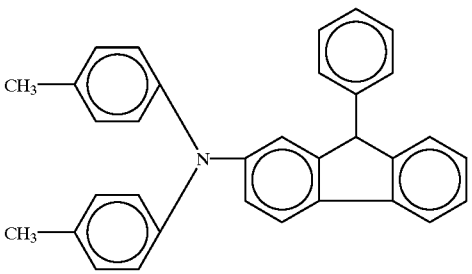
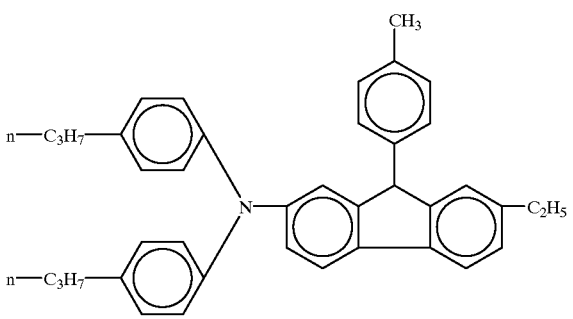
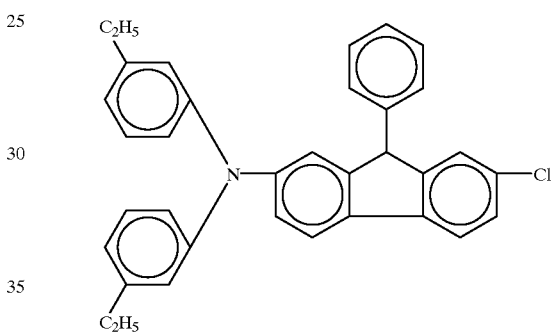
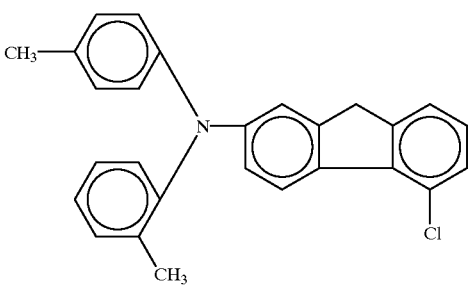
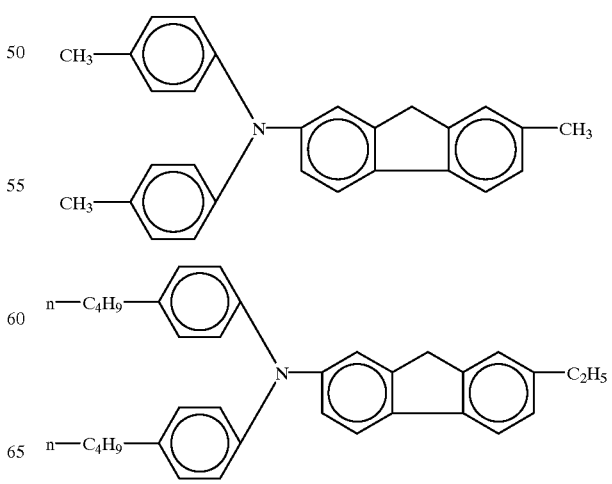

-continued

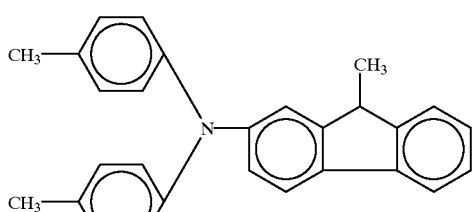

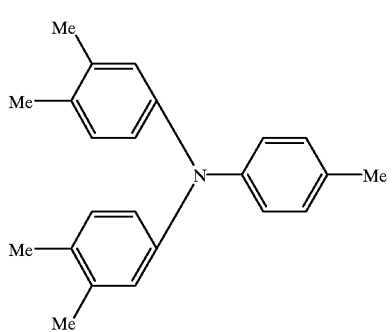

(oxidation potential: 0.78 V)
ionization potential: 5.43 eV

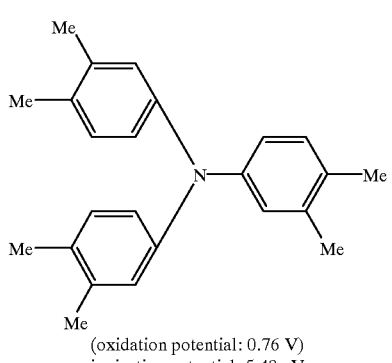

(oxidation potential: 0.76 V)
ionization potential: 5.40 eV

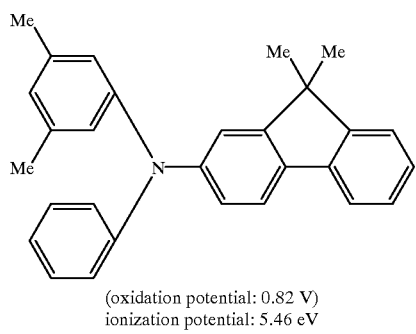

(oxidation potential: 0.82 V)
ionization potential: 5.46 eV

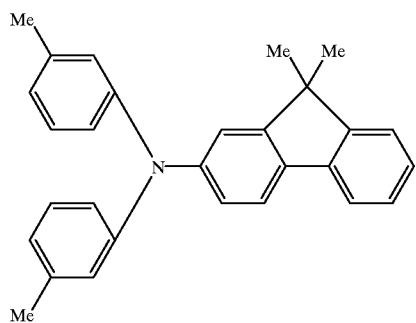

(oxidation potential: 0.82 V)
ionization potential: 5.45 eV

-continued

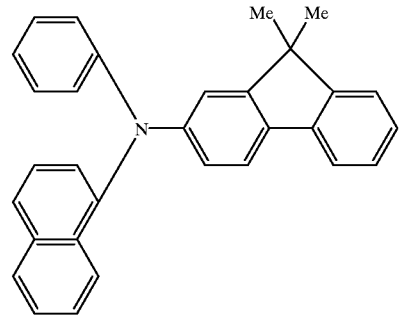

(oxidation potential: 0.89 V)
ionization potential: 5.52 eV

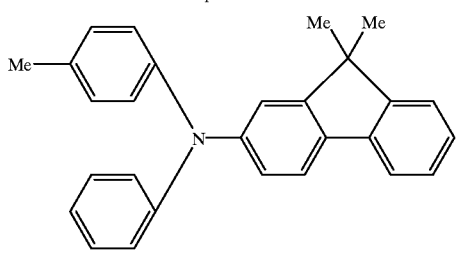

(oxidation potential: 0.81 V)
ionization potential: 5.45 eV

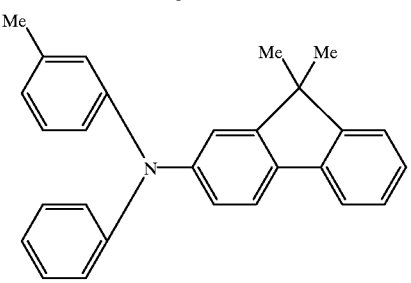

(oxidation potential: 0.84 V)
ionization potential: 5.47 eV

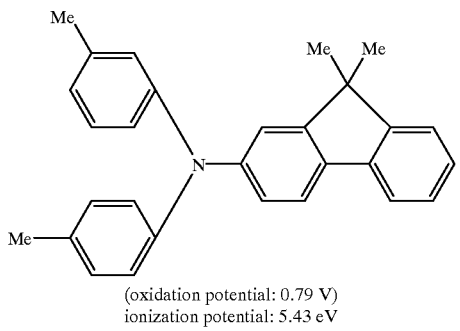

(oxidation potential: 0.79 V)
ionization potential: 5.43 eV

Triphenylmethane type:

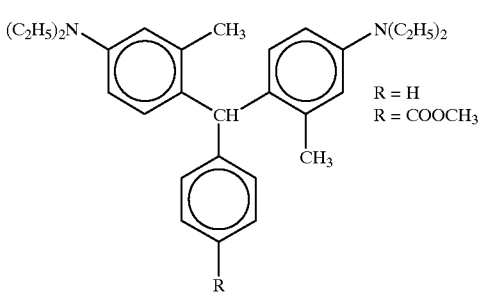

R = H
R = COOCH$_3$

Styryl, stilbene type:

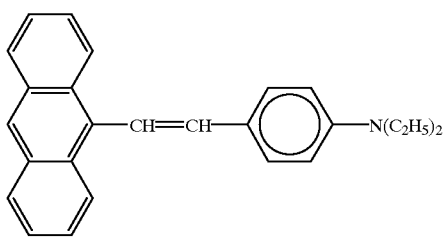

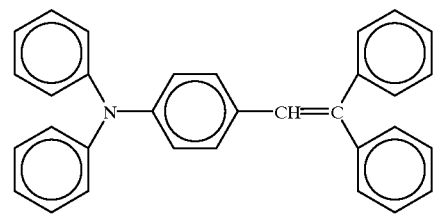

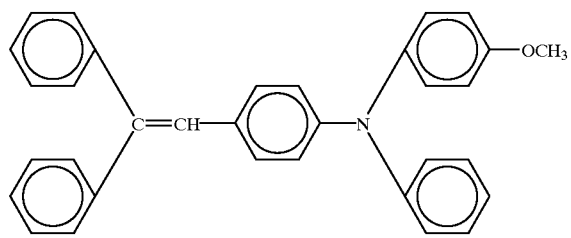

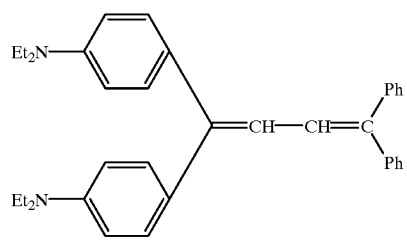

(oxidation potential: 0.50 V)
ionization potential: 5.15 eV

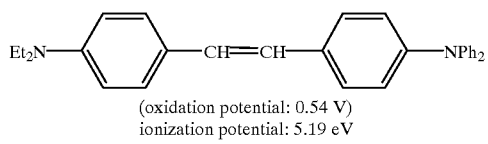

(oxidation potential: 0.54 V)
ionization potential: 5.19 eV

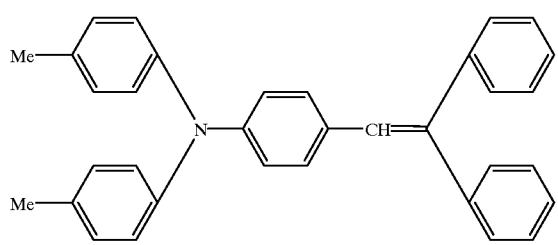

(oxidation potential: 0.76 V)
ionization potential: 5.40 eV

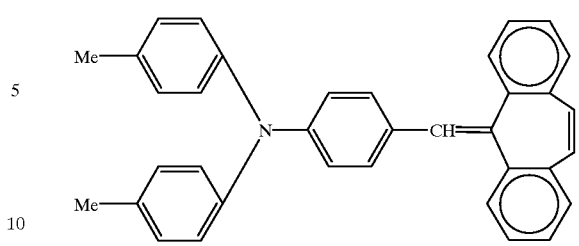

(oxidation potential: 0.81 V)
ionization potential: 5.45 eV

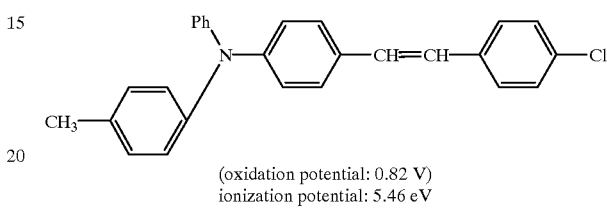

(oxidation potential: 0.82 V)
ionization potential: 5.46 eV

Enamine type:

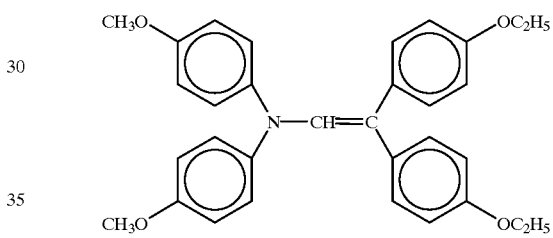

The hydrogenated charge transporting group A compound. can be synthesized by the following method. Synthesis of

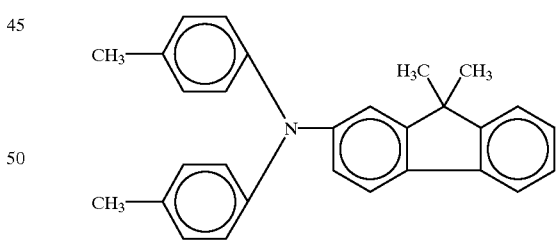

To 20 ml of nitrobenzene, 10.0 g of 2-amino-9,9-dimethylfluorene, 36.1 g (165.6 mmol) of p-iodotoluene, 22.9 g (165.7 mmol) of anhydrous potassium carbonate and 7.0 g of copper powder were added, followed by heating and reflux for 8 hours with stirring. After the reaction mixture obtained was left to cool, it was suction-filtrated and the obtained filtrate was evaporated under reduced pressure. The residue was subjected to silica gel column chromatography for purification to obtain 15.6 g of the title compound. m.p.: 141.0 to 141.5° C.

Synthesis of

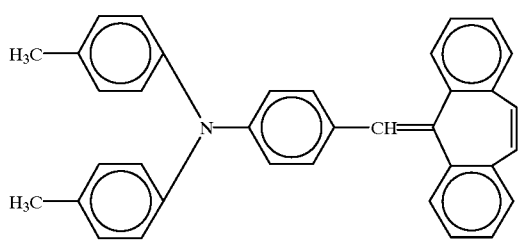

I. MA reaction:

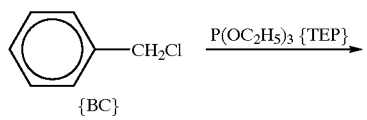

II. Nitrogenation reaction:

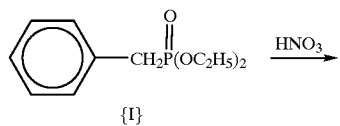

III. Wittig reaction:

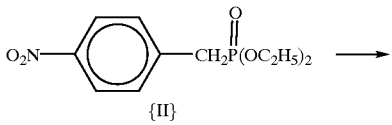

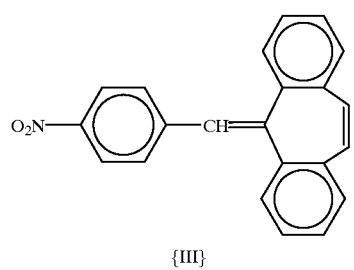

IV. Reduction reaction:

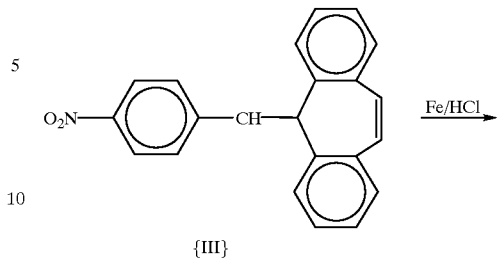

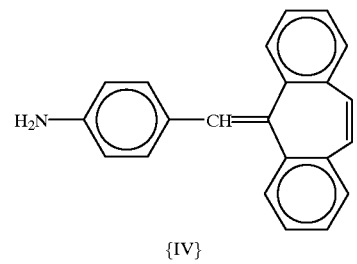

V. Ulmann reaction:

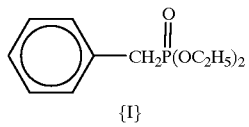

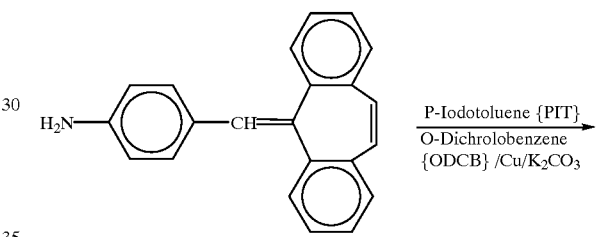

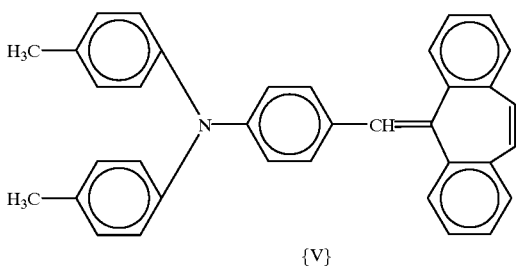

A mixture of 154 ml (1.34 mol) of benzyl chloride (d=1.10) and 206 ml (1.2 mol) of triethyl phosphite (d=0.969) were gradually heated with stirring in an oil bath. The oil bath was kept at around 160 to 180° C. and refluxed and stirred for 20 hours. After the reaction was completed, the reaction mixture was distilled under reduced pressure to obtain 215.4 g of diethylbenzyl phosphonate. Yield: 78.6%; b.p.: 134.6 to 135.0° C. (7 mmHg).

Next, into a 200 ml three-necked flask, 55.0 ml (1.25 mol) of fuming nitric acid (d=1.52, 94%) was placed, and cooled to the inner temperature of −10 to −5° C. with stirring. Thereafter, 61.6 g (0.27 mol) of the diethylbenzyl phosphonate previously obtained was slowly added dropwise over 1 hour. After the addition was completed, the reaction mixture was stirred for 30 minutes at the same temperature, and thereafter it was poured in about 600 ml of ice water, followed by extraction with about 300 ml of ethyl acetate. The organic layer was washed with saturated brine and dried with anhydrous sodium sulfate before evaporation under reduced pressure. The residue was subjected to distillation under reduced pressure to obtain 61.3 g of diethyl-4-nitrobenzyl phosphonate. Yield: 83.1%; b.p.: 199 to 201.0° C. (3 mmHg).

Elemental analysis gave $C_{11}H_{16}NO_5$:

|  | C (%) | H (%) | N (%) |
|---|---|---|---|
| Calculated: | 48.36 | 5.90 | 5.13 |
| Found: | 48.39 | 5.92 | 5.40 |

To 150 ml of dimethylsulfoxide, 3.60 g (about 90 mmol) of oily sodium hydride (about 60%) was added at room temperature. After the addition, the mixture was heated to the inner temperature of around 70° C. in an oil bath, and stirred under the same conditions for 1 hour. Thereafter, the reaction solution was cooled to room temperature, and then a solution of 25.1 g (92 mmol) of the diethyl-4-nitrobenzyl phosphonate and 10.0 g (48.6 mmol) of 5H-dibenzo[a,d]cyclohepten-5-one in 50 ml dimethyl sulfoxide was added dropwise thereto. After the addition was completed, the resulting mixture was stirred for 15 minutes at room temperature, and thereafter heated and stirred for 2 hours in an oil bath while keeping its internal temperature at 70 to 80° C. After the reaction was completed, the reaction mixture was cooled to room temperature, and then poured in about 1 liter of saturated brine, followed by extraction with ethyl acetate. The organic layer was dried with anhydrous sodium sulfate, and the solvent was removed under reduced pressure. To the residue thus obtained was added methanol, and the precipitated crystals were collected by filtration. The crystals were then recrystallized using a methanol/acetone mixed solvent to obtain 10.94 g of 5-(4-nitrobenzylidene)-5H-dibenzo[a,d]cycloheptene. Yield: 69.3%; m.p.: 151.5 to 152.5° C.

Elemental analysis gave $C_{22}H_{16}NO_2$:

|  | C (%) | H (%) | N (%) |
|---|---|---|---|
| Calculated: | 81.21 | 4.65 | 4.30 |
| Found: | 81.18 | 4.69 | 4.31 |

To 150 ml of N,N-dimethylformamide, were added 10.0 g (30.7 mmol) of the above 5-(4-nitrobenzylidene)-5H-dibenzo[a,d]cycloheptene, 8.0 g (143 mmol) of reduced iron powder and 2.70 ml (30.6 mmol) of concentrated hydrochloric acid (d=1.18, 35%). The resulting mixture was heated to the inner temperature of about 70° C., and then heated and stirred for 3 hours at the same temperature. After the reaction was completed, the reaction mixture was cooled in an ice water bath, and about 12.4 ml of an aqueous 10% sodium hydroxide solution was added thereto, followed by stirring and thereafter suction filtration. The filtrate obtained was poured in about 1 liter of saturated brine, and extracted with ethyl acetate. The organic layer was dried with anhydrous sodium sulfate, and the solvent was removed under reduced pressure. To thus obtained residue was added methanol, and the crystals precipitated were collected by filtration. The crystals were then recrystallized from methanol to give 8.41 g of 5-(4-aminobenzylidene)-5H-dibenzo[a,d]cycloheptene. Yield: 92.7%; m.p.: 119 to 120.0° C.

Elemental analysis gave $C_{22}H_{17}N$:

|  | C (%) | H (%) | N (%) |
|---|---|---|---|
| Calculated: | 89.46 | 5.80 | 4.74 |
| Found: | 89.41 | 5.83 | 4.76 |

To 30 ml of o-dichlorobenzene, were added 7.90 g (26.7 mmol) of the 5-(4-aminobenzylidene)-5H-dibenzo[a,d]cycloheptene previously obtained, 22.0 g (101 mmol) of p-iodotoluene, 11.0 g (79.6 mmol) of anhydrous sodium carbonate and 2.2 g of copper powder. The mixture was refluxed with stirring for 7 hours in an oil bath kept at around 190° C. After the reaction was completed, the reaction was subjected to suction filtration and the filtrate was successively washed with an aqueous 35% sodium thiosulfate solution and saturated brine. The organic layer was dried with anhydrous sodium sulfate, and the solvent was removed under reduced pressure. To the resulting residue was added about 60 ml of acetone, and the precipitated crystals were collected by filtration. The crystals obtained were further recrystallized using an ethyl acetate/n-hexane mixed solvent to obtain 9.52 g of 5-[4-(di-p-tolylamino)benzylidene)-5H-dibenzo[a,d]cyclo heptene. Yield: 75.0%; m.p.: 168.0 to 169.0° C.

Elemental analysis gave $C_{36}H_{29}N$:

|  | C (%) | H (%) | N (%) |
|---|---|---|---|
| Calculated: | 90.90 | 6.15 | 2.96 |
| Found: | 90.86 | 6.17 | 2.98 |

Preferred examples of the organosilicon-modified charge transporting compound of the present invention are shown below.

Triphenylamine type:

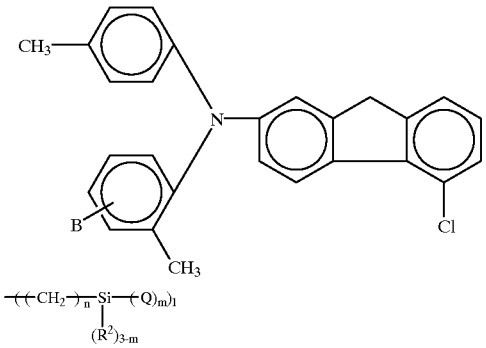

$B = -((CH_2)_n-Si-(Q)_m)_l$
$\phantom{B = -((CH_2)_n-}(R^2)_{3-m}$ wherein Q represents a hydrolytic group or a hydroxyl group, $R^2$ represents a monovalent hydrocarbon group or a halogen-substituted monovalent hydrocarbon group of 1 to 15 carbon atoms, n is 1 to 18, m is 1 to 3, and l is 1 to 5. (The same applies hereinafter.)

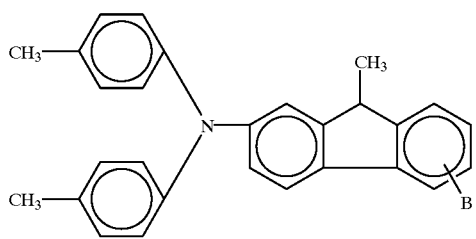
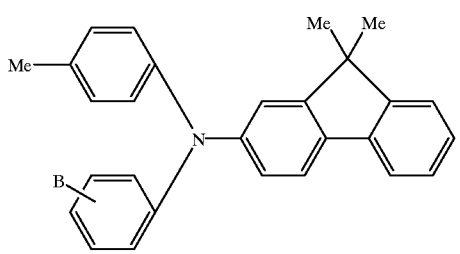
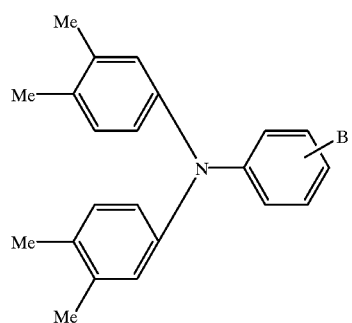
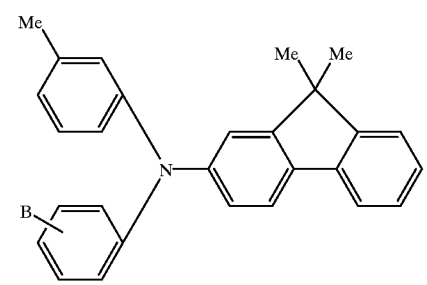
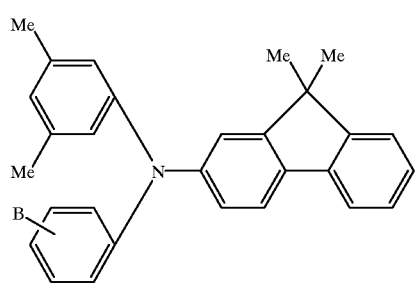
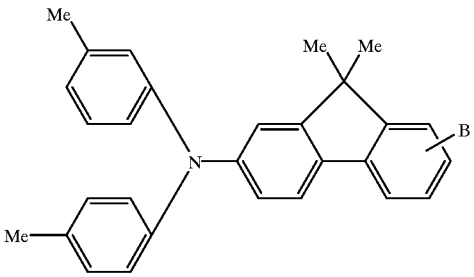
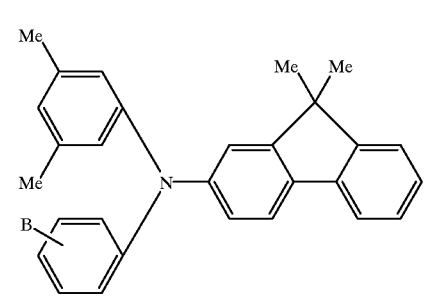
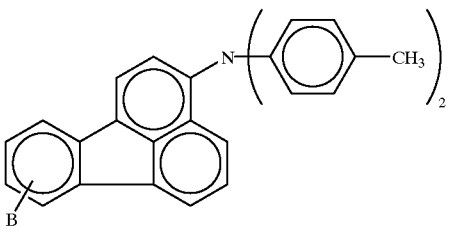
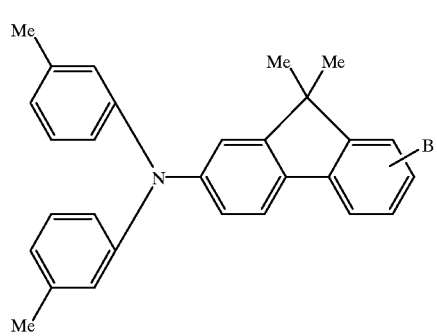
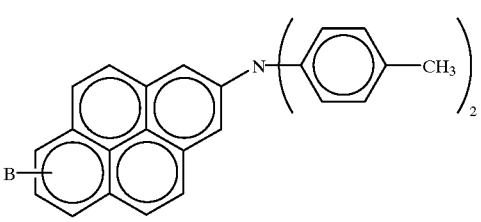
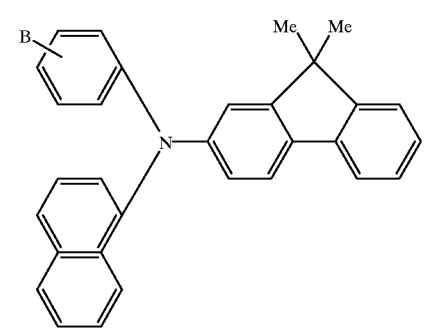
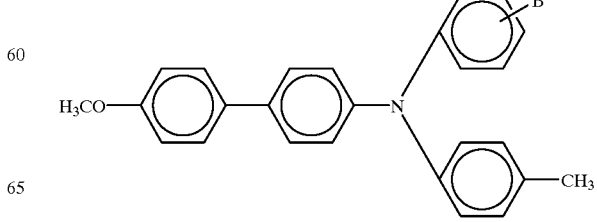

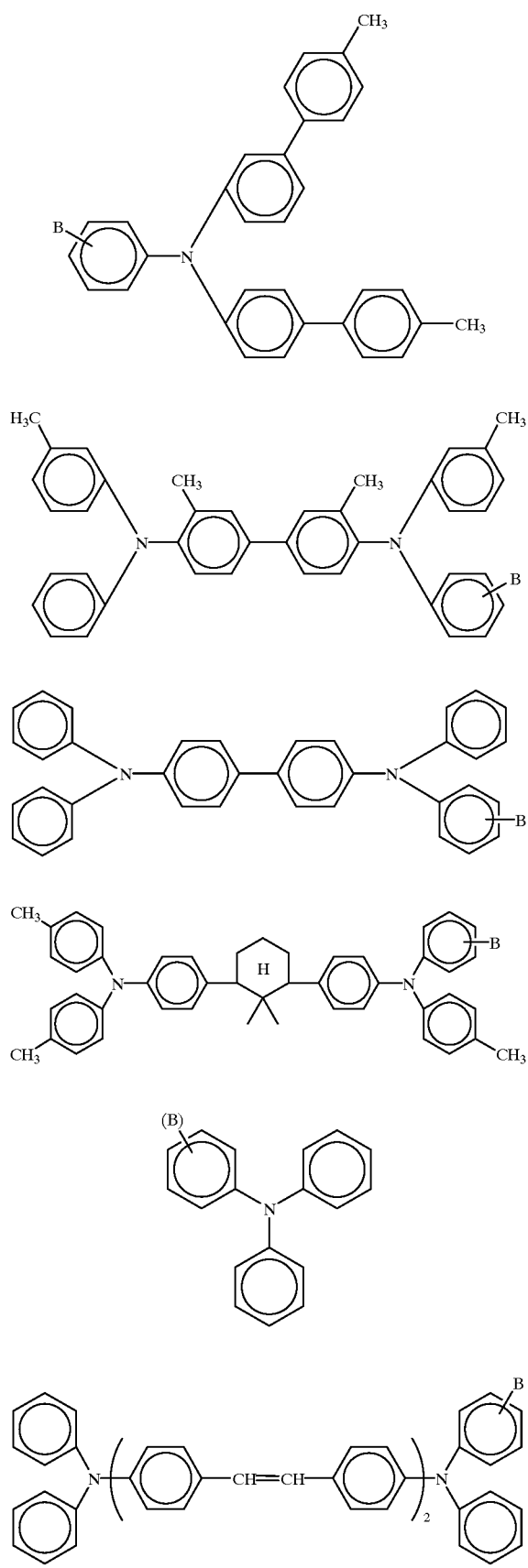
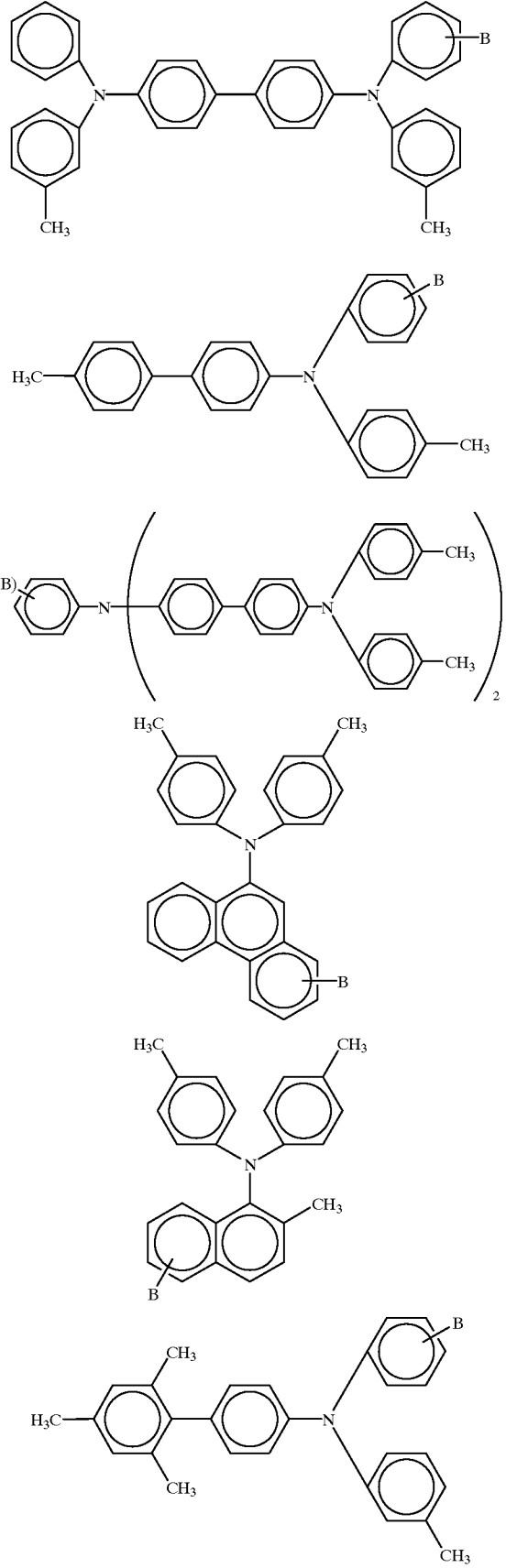

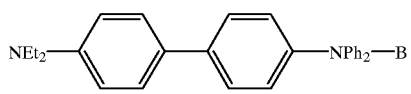
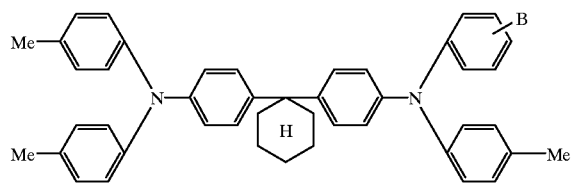
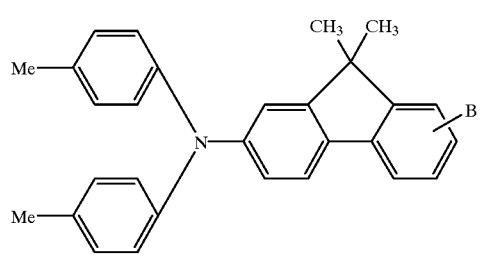
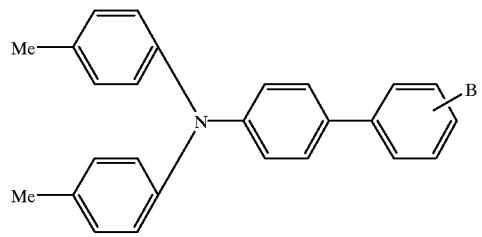
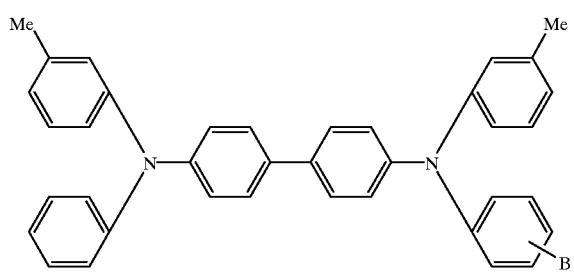
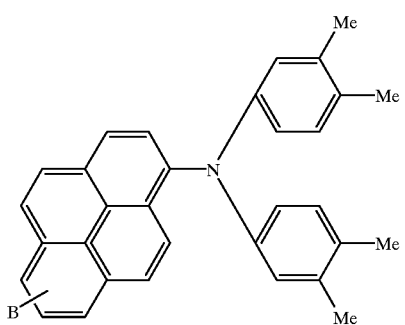
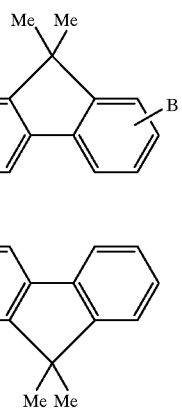
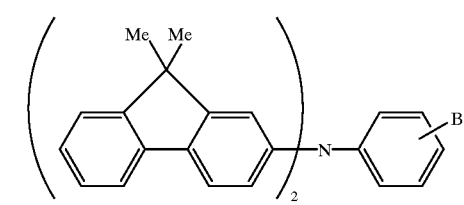
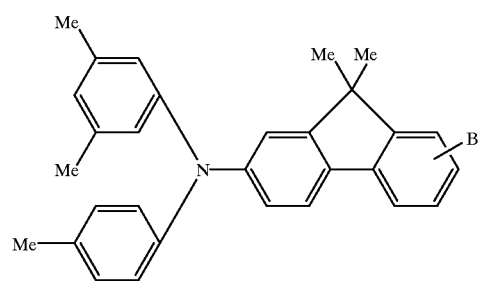
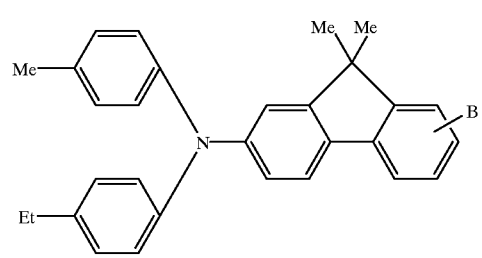
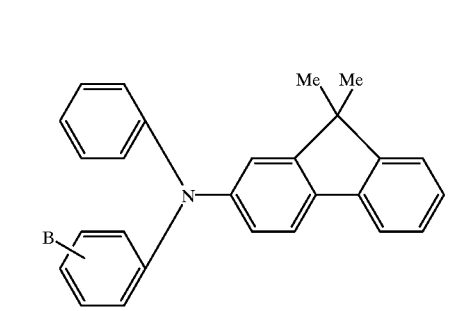

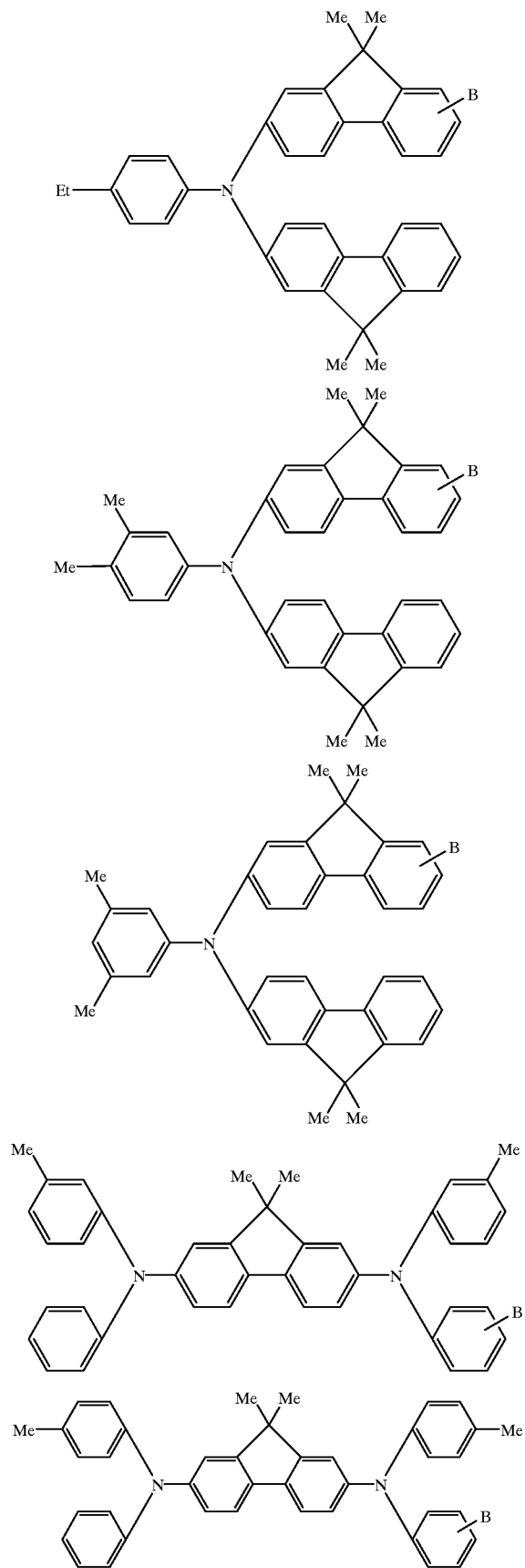
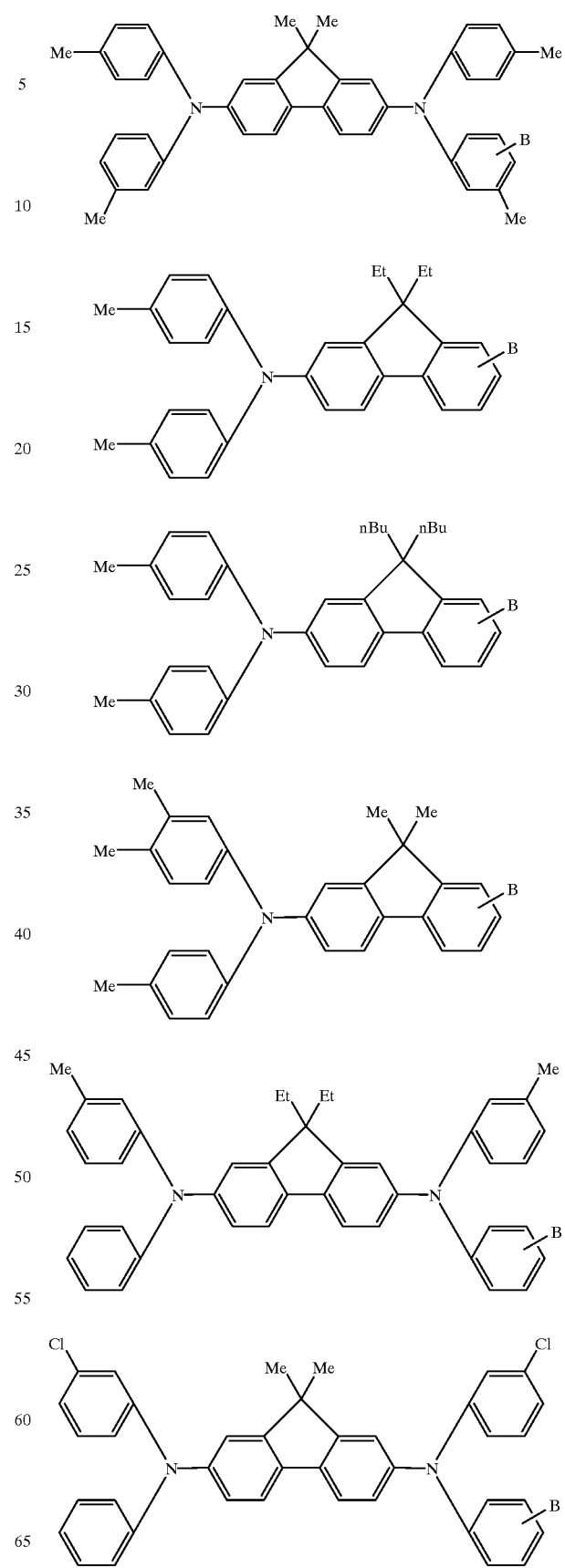

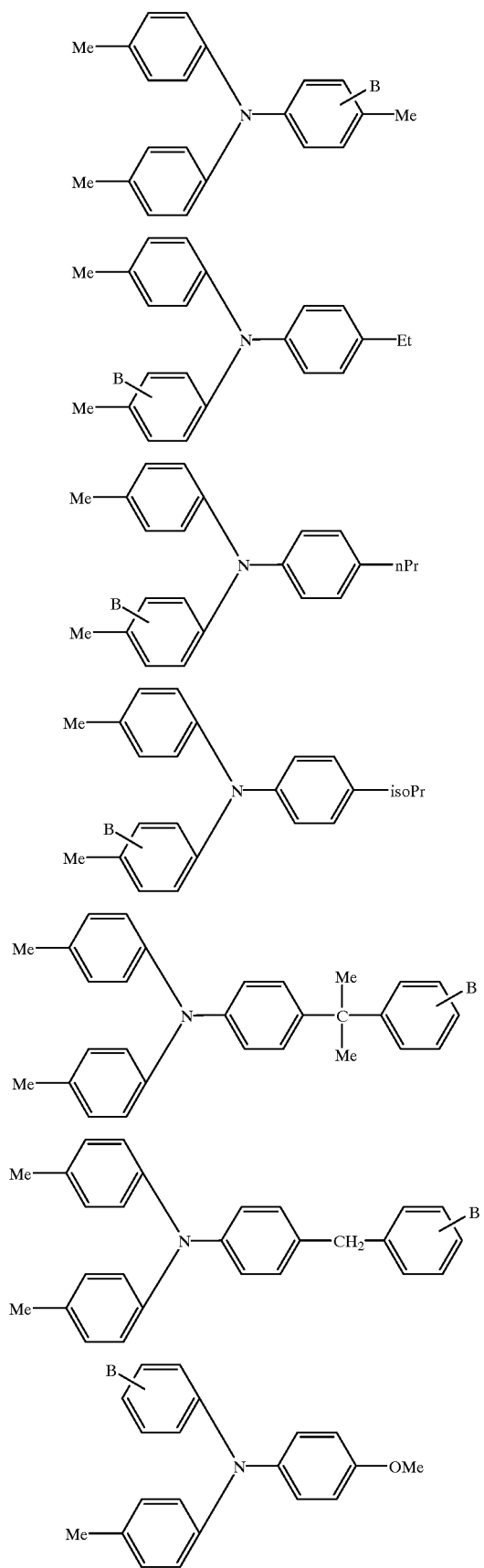
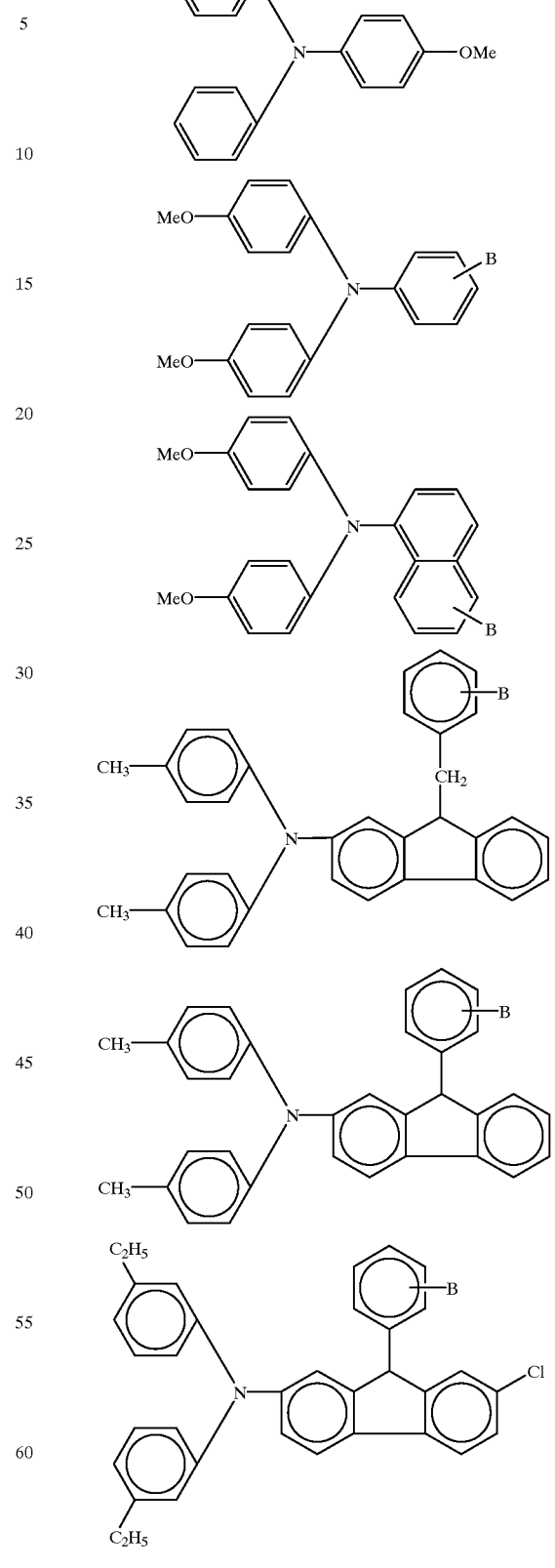
The above organosilicon-modified charge transporting compound represented by Formula (I) can be synthesized by known methods. For example, preferably used is a method for hydrosilylation between a compound having a vinyl group on an aromatic ring and a hydrogenated silicon compound having a substituent in the presence of a platinum catalyst or an organic peroxide as a catalyst. There are no particular limitations on the platinum catalyst to be used, and any platinum catalysts used in usual hydrosilylation and addition type silicone rubber synthesis can be used, including platinum chloride, chloroplatinic acid, platinum-olefin complexes and platinum-phosphine complexes. There are no particular limitations on the amount of the platinum catalyst to be added. It is preferable for the catalyst to be used in an amount as small as possible so that any residual catalyst may not adversely affect the properties of the product.

When the compound of the present invention is synthesized from a compound having a vinyl group on an aromatic ring and a hydrogenated silicon compound having a substituent, by addition reaction in the presence of the platinum catalyst, reaction occurs at the α-position or at the β-position of the vinyl group, and usually a mixture is produced. In the present invention, either those having reacted at the α-position or those at the β-position may be used. When the number of carbon atoms of the hydrocarbon group which links the silicon atom and the charge transporting group is small, compounds having reacted at the β-position are preferred to avoid steric hindrance.

As the organic peroxide, those having a half-life at room temperature or above may be used. In particular, alkyl peroxides such as lauryl peroxide may preferably be used because it may hardly cause the pull-out of hydrogen. As for a compound having no vinyl group, a vinyl group can be introduced to the aromatic ring, for example, by formylation followed by reduction or dehydration, or directly by Wittig reaction, thus it can be used as the starting material in the present invention.

Next, the curable resin which is contained in the curable composition having the charge transporting ability of the second present invention, will be described.

The organosilicon high polymer, the chief component of the cure type resin, is exemplified by organopolysiloxanes, polysilalkylenesiloxanes and polysilarylenesiloxanes, where the number ratio of the monovalent hydrocarbon groups bonded to silicon atoms and the silicon atoms is from 0.5 to 1.5. As this ratio becomes smaller than 1.0, the polymer becomes compositionally close to glass to cause less weight loss by heating and the resin product tends to be harder, and if the ratio is less than 0.5, it is difficult to make into films. On the other hand, as this ratio becomes larger than 1.0, the polymer shows an opposite tendency. For example, organopolysiloxanes become polydiorganopolysiloxanes at the ratio of 2.0. Thus, if the ratio is more than 1.5, the polymer becomes too rubbery, resulting in hardness deficiency.

The organopolysiloxane may preferably include those having a structural unit represented by the following Formula (III).

$$R^6{}_n SiO_{(4-n-m)/2}(OR^7)_m \qquad (III)$$

wherein $R^6$ represents a straight-chain or branched alkyl or alkenyl group having 1 to 18 carbon atoms, or an aryl group; $R^7$ represents an alkyl group having 1 to 4 carbon atoms; n is 0.5 to 1.5 on average; and m is 0.01 to 1.5 on average.

The straight-chain or branched alkyl group having 1 to 18 carbon atoms of $R^6$ may include a methyl group, an ethyl group, a propyl group, a butyl group, a pentyl group, a hexyl group, a 2-ethylhexyl group, a dodecyl group and an octadecyl group; the alkenyl group may include, e.g., a vinyl group and an allyl group; and the aryl group may include a phenyl group and a tolyl group. $R^6$ may further include halogen-substituted, straight-chain or branched saturated hydrocarbon groups having 1 to 18 carbon atoms such as fluorohydrocarbon groups as typified by a trifluoropropyl group, a heptafluoropentyl group and a nonafluorohexyl group, chlorohydrocarbon groups as typified by a chloromethyl group and a chloroethyl group.

$R^6$ need not to be a single type, and is selected according to what to be improved, e.g., resin properties, and solubility of resin in solvent. It is well-known in the art that when a system has both methyl and phenyl groups, usually it has more affinity for organic compounds than a system having methyl groups only. When the fluorohydrocarbon group is introduced into an organopolysiloxane, surface tension decreases due to the fluorine atom as with other high polymers, so that properties of such as water repellency and oil repellency may be changed. Also in the present invention, when a lower surface tension is required, a silicon unit bonded to a fluorohydrocarbon group may be introduced by copolymerization.

In the above Formula (III), the $OR^7$ group bonded to the silicon atom represents a hydroxyl group or a group capable of hydrolysis condensation. $R^7$ is selected from a hydrogen atom and lower alkyl groups such as methyl, ethyl, propyl and butyl. The reactivity of $R^7$ in the $OR^7$ group, highest when $R^7$ is hydrogen, decreases as the number of carbon atoms of the alkyl group increases, and $R^7$ may be appropriately selected according to the reaction system used. The number of the group capable of hydrolysis condensation is represented by m. So long as m is 0.01 or more, this group can serve in the cross-linking of the present resin. As well known, the hardness of a resin is adjusted by controlling the crosslinking density. In the present invention too, the hardness of the resin can be controlled by the number of the above group capable of hydrolysis condensation bonded to the silicon atom. If, however, the number of the group capable of hydrolysis condensation is too large, unreacted groups may remain in the system so that they may be hydrolyzed in the use environment, thus adversely affecting surface properties. Preferred values of m are 0.01 to 1.5.

As one of the common features, organosilicon high polymers have very poor affinity for or solubility in organic compounds. For example, antioxidants, ultraviolet light absorbents and so forth which are used in ordinary organic resins have no solubility in dimethylpolysiloxane and agglomerate in it. Conventional charge transporting compounds are no exception, and it is difficult to dissolve them at such a concentration of effective charge transport. The charge transporting compound represented by Formula (I) and the above mentioned organosilicon high polymer, in particular organopolysiloxane, have a good compatibility, enabling remarkable improvement in mechanical properties.

The above mentioned cure type resin may also be cross-linked by adding a cross-linking agent at the time of curing.

The above mentioned cure type resin may also contain a cross-linking agent, a silane compound represented by the following Formula (IV). This makes it easy to control physical properties such as hardness and strength of the surface protective layer obtained by curing the curable composition.

$$R^8{}_a SiX_{4-a} \qquad (IV)$$

wherein $R^8$ represents a straight-chain or branched alkyl or alkenyl group having 1 to 18 carbon atoms, or a phenyl group; X represents a hydrolyzable group; and a represents a molar ratio to Si.

In Formula (IV), the group represented by $R^8$ may include a methyl group, an ethyl group, a propyl group, a butyl group, an amyl group, a hexyl group, a vinyl group, an allyl group, a phenyl group and a tolyl group. The hydrolytic group represented by X may include a hydrogen atom, a methoxy group, an ethoxy group, a methyl ethyl ketoxime group, a diethylamino group, an acetoxy group, a propenoxy group, a propoxy group and a butoxy group.

For the above crosslink curing of the resin, addition of a catalyst is not necessary, but if used, an ordinary catalyst used for curing of conventional organosilicon high polymers may be used, appropriately selected from alkyltin organic acid salts such as dibutyltin diacetate, dibutyltin dilaurate and dibutyltin octoate, or organic titanates such as n-butyl titanate, taking account of the curing time, the curing temperature and so forth.

As examples of the silane compound represented by Formula (IV), which serves as the cross-linking agent, it may include methyltrimethoxysilane, methyltriethoxysilane, vinyltrimethoxysilane, phenyltriethoxysilane, and silanes having, in place of these alkoxy group, an acetoxy group, e.g. a methyl. ethyl ketoxime group, a diethylamino group or an isopropenoxy group. The cross-linking agent may be in the form of an oligomer such as ethyl polysilicate.

The organosilicon high polymer used in the present invention can be produced by known methods including the method disclosed in Japanese Patent Publication No. 26-2696 and No. 28-6297, and the organopolysiloxane synthesis method described in Chemistry and Technology of Silicones, Chapter 5, p.191 (Walter Noll, Academic Press, Inc., 1968). For example, an organoalkoxysilane or organohalogenosilane, of which substitution number n of monovalent organic groups to the silicon atom is 0.5 to 1.5 on average, is dissolved in an organic solvent, and then hydrolyzed and condensed in the presence of an acid or base to carry out polymerization, followed by removal of the solvent. The organosilicon high polymer used in the present invention is dissolved in a solvent which includes aromatic hydrocarbons such as toluene and xylene, aliphatic hydrocarbons such as cyclohexanone and hexane, halogen-containing hydrocarbons such as chloroform and chlorobenzene, and alcohols such as ethanol and butanol.

The curable composition of the present invention, comprising a cure type resin chiefly composed of an organosilicon high polymer and an organosilicon-modified charge transporting compound can be prepared by, for example, mixing them in a solvent capable of dissolving both. The organosilicon-modified charge transporting compound may preferably be mixed in an amount of from 20 to 200 parts by weight based on 100 parts by weight of the cure type resin as solid matter not containing the solvent. Its use in an amount less than 20 parts by weight is not preferable because charge transporting properties become insufficient and charge potential is increased. Its use in an amount more than 200 parts by weight is also not preferable because the mechanical strength decreases and surface energy increases. The organosilicon-modified charge transporting compound may more preferably be used in an amount of from 30 to 150 parts by weight based on 100 parts by weight of the cure type resin.

In the curable composition of the present invention, the cure type resin can be partly reacted with the organosilicon-modified charge transporting compound before hand, so long as it is in the form of a solution or dispersion which allows its application on a photosensitive member followed by curing.

As the conditions of curing, the composition may preferably be heated at 100 to 200° C. If the heating temperature is below 100° C., the curing reaction takes a long time, and hence there is a possibility that unreacted hydrolytic groups remain. If the heating temperature is above 200° C., the charge transporting group tends to deteriorate by oxidation with an undesirable effect. More preferably, the composition is heated for curing at 120 to 160° C. for the use.

The curable composition of the present invention having a charge transporting ability can be used to form a surface protective layer having a charge transporting ability upon curing.

In the curable composition of the present invention having a charge transporting ability, additives may be used besides the above compounds in order to improve mechanical properties and improve durability. The additives that may be used include antioxidants, ultraviolet light absorbents, stabilizers, lubricants and conductivity-controlling agents.

The curable composition of the present invention having a charge transporting ability can be used as a surface protective layer having a high hardness and a small surface energy. When used in such a way, it is used so that the surface protective layer has a thickness of from 0.5 to 50 $\mu$m. If it is thinner than 0.5 $\mu$m, no sufficient protective effect can be obtained, and if thicker than 50 $\mu$m, the cost undesirably increases.

EXAMPLES

The present invention will be described below in greater detail by giving Examples.

Cure Type Resin Chiefly Composed of Organopolysiloxane

Reference Example 1
Preparation of Solution of Cure Type Resin Chiefly Composed of Methylpolysiloxane Resin:

In 10 g of toluene, was dissolved 10 g of methylpolysiloxane resin containing 1% by weight of silanol groups and comprised of 80 mol % of methylsiloxane units and 20 mol % of dimethylsiloxane units. To the resulting solution, 5.3 g of methyltrimethoxysilane and 0.2 g of dibutyltin diacetate were added to make a uniform solution.

Reference Example 2
Preparation of Solution of Cure Type Resin Chiefly Composed of Methylpolysiloxane Resin:

In 10 g of toluene, was dissolved 10 g of methylpolysiloxane resin containing 1% by weight of a silanol group and comprised of 80 mol % of methylsiloxane units and 20 molt of dimethylsiloxane units. To the solution obtained, 11.5 g of methyltri(methylethyl ketoxime)silane and 0.2 g of dibutyltin diacetate were added to make a uniform solution.

Reference Example 3
Preparation of Solution of Cure Type Resin Chiefly Composed of Methylphenylpolysiloxane Resin:

In 10 g of toluene, was dissolved 12 g of methylphenylpolysiloxane resin containing 1% by weight of a silanol group and comprised of 40 mol % of phenylsiloxane unit, 20 mol % of diphenylsiloxane unit, 20 mol % of methylsiloxane and 20 mol % of dimethylsiloxane unit, followed by addition of 0.2 g of dibutyltin diacetate to make a uniform solution.

Reference Example 4
Preparation of Solution of Cure Type Resin Chiefly Composed of Fluorosilicone Resin:

In 10 g of toluene, was dissolved 11 g of methylnonafluorohexyl-polysiloxane resin containing 1% by weight of a silanol group and comprised of 50 mol % of methylsiloxane unit, 10 mol % of dimethylsiloxane unit and 10 mol % of 3,4,4,5,5,6,6,6-nonafluorohexylsiloxane unit. To the resulting solution, 0.2 g of dibutyltin diacetate was added to make a uniform solution.

Examples Concerning Organosilicon-modified Charge Transporting Compound

Example 1

Synthesis of 4-[2-(triethoxysilyl)ethyl]tri-phenylamine:

Synthesis of 4-(N,N-diphenylamino)benzaldehyde

Into a three-necked flask, 101.4 g of triphenylamine and 35.5 ml of DMF (dimethylformamide) were placed, and 84.4 ml of phosphorus oxychloride was added dropwise thereto with stirring while cooling with ice water, and then the temperature was raised to 95° C. to carry out reaction for 5 hours. The reaction solution obtained was poured into 4 liters of warm water, followed by stirring for 1 hour. Thereafter, the precipitate formed was collected by filtration, and washed with a mixture of ethanol/water (1:1) to obtain 4-(N,N-diphenylamino)benzaldehyde in an amount of 91.5 g (yield: 81.0%).

Synthesis of 4-vinyltriphenylamine

Into a three-necked flask, 14.6 g of sodium hydride and 700 ml of 1,2-dimethoxyethane were placed, and 130.8 g of trimethylphosphonium bromide was added thereto with stirring at room temperature. Next, after a drop of absolute alcohol was added, the reaction was allowed to proceed at 70° C. for 4 hours. Then, 100 g of 4-(N,N-diphenylamino) benzaldehyde was added thereto, and the temperature was raised to 70° C. to carry out reaction for 5 hours. The resulting reaction solution was filtered, and the filtrate and an ether-extract of the precipitate were put together and washed with water. Then, the ether solution was dehydrated with calcium chloride, and ether was removed to obtain a crude reaction product. After recrystallized from ethanol, acicular pale yellow vinyltriphenylamine was obtained in an amount of 83.4 g (yield: 84.0%).

Hydrosilylation of 4-vinyltriphenylamine

Into a three-necked flask, 40 ml of toluene, 9.9 g (60 mmol) of triethoxysilane and 0.018 mmol of diplatinum (0) tris(tetramethyl-divinyldisiloxane) in toluene were placed, and 20 ml of a toluene solution containing 8.2 g of 4-vinyltriphenylamine was added dropwise with stirring at room temperature. After the addition was completed, the mixture was stirred at 70° C. for 3 hours, and thereafter the solvent was removed under reduced pressure to obtain oily pale yellow 4-[2-(triethoxysilyl)ethyl]triphenylamine in an amount of 12.1 g (yield: 91.7%).

An H-NMR spectrum (measured by APC300, an NMR spectrometer manufactured by Bruker Co.) of the compound is shown in FIG. 1.

Ionization potential of this compound measured by atmospheric photoelectron analysis (using a surface analyzer AC-1, manufactured by Riken Keiki K.K.) was 5.68 eV.

Example 2

Synthesis of 4-[2-(methyldiethoxysilyl)ethyl]-triphenylamine:

Hydrosilylation of 4-vinyltriphenylamine

Into a three-necked flask, 40 ml of toluene, 8.1 g of methyldiethoxysilane and 0.018 mmol of diplatinum (0) tris(tetramethyldivinyl-disiloxane) in toluene were placed, and 20 ml of a toluene solution containing 8.2 g of 4-vinyltriphenylamine was added dropwise with stirring at room temperature. After the addition was completed, the mixture was stirred at 70° C. for 3 hours, and thereafter the solvent was removed under reduced pressure to obtain oily pale yellow 4-[2-(methyldiethoxysilyl)ethyl]triphenylamine in an amount of 11.2 g (yield: 91.4%).

Ionization potential of this compound measured by atmospheric photoelectron analysis (using a surface analyzer AC-1, manufactured by Riken Keiki K.K.) was 5.66 eV.

Example 3

Synthesis of 4,4',4"-tris[2-(triethoxysilyl)-ethyl] triphenylamine:

Synthesis of tri-(4-formylphenyl)amine

Into a three-necked flask, 50.7 g of triphenylamine and 53.3 ml of DMF were placed, and 126.6 ml of phosphorus oxychloride was added dropwise thereto with stirring while cooling with ice water. After the addition was completed, the mixture solution was heated to 95° C. to carry out reaction for 5 hours. The reaction solution obtained was poured into 5 liter of warm water, followed by stirring for 1 hour. Thereafter, the precipitate formed was collected by filtration, and washed with a mixture of ethanol/water (1:1) to obtain tri-(4-formylphenyl)amine in an amount of 65.3 g (yield: 95.9%).

Synthesis of tri(4-vinylphenyl))amine

Into a three-necked flask, 14.6 g of sodium hydride and 70 ml of 1,2-dimethoxyethane were placed, and 130.8 g of trimethylphosphonium bromide was added thereto with stirring at room temperature. Next, after a drop of absolute alcohol was added, the reaction was allowed to proceed at 70° C. for 4 hours. Then, 40.2 g of (4-formylphenyl)amine was added to the mixture thus obtained, to carry out reaction at 70° C. for 5 hours. The reaction solution obtained was filtered to remove the cake. The ether extract of the cake was put together with the filtrate, and washed with water. Then, the ether solution was dehydrated with calcium chloride, and thereafter ether was removed to obtain a reaction mixture. After twice recrystallization with ethanol, acicular pale yellow tri(4-vinylphenyl)amine was obtained in an amount of 38.4 g (yield: 97.3%).

Hydrosilylation of tri(4-vinylphenyl)amine

Into a three-necked flask, 40 ml of toluene, 9.9 g (60 mmol) of triethoxysilane and 0.018 mmol of diplatinum (0) tris(tetramethyl-divinyldisiloxane) in toluene were placed, and 20 ml of a toluene solution containing 3.3 g (13 mmol) of tri(4-vinylphenyl)amine was added dropwise with stirring at room temperature. After the addition was completed, the mixture was stirred at 70° C. for 3 hours, and thereafter the solvent was removed under reduced pressure to obtain oily pale yellow 4,4',4"-tris[2-(triethoxysilyl)ethyl]triphenylamine in an amount of 7.8 g (yield: 80.6%).

Ionization potential of this compound measured by atmospheric photoelectron analysis (using a surface analyzer AC-1, manufactured by Riken Keiki K.K.) was 5.65 eV.

Example 4

Synthesis of 4-[N,N-bis(3,4-dimethylphenyl)amino]-[2-(triethoxysilyl)ethyl]benzene:

Synthesis of N,N-bis(3,4-dimethylphenyl)amino-benzene

To 20 ml of nitrobenzene, 38.5 g (166 mmol) of 4-iodo-o-xylene, 22.9 g (166 mmol) of anhydrous potassium carbonate and 7.0 g of copper powder were added, followed by heating and reflux for 8 hours with stirring. The reaction mixture was cooled and filtered, and the precipitate was removed. The filtrate (crude reaction product) was passed through a silica gel column to obtain 15.7 g of N,N-bis(3, 4-dimethylphenyl)aminobenzene (yield: 69%).

Synthesis of 4-[N,N-bis(3,4-dimethylphenyl)-amino] benzaldehyde

Into a three-necked flask, 124.6 g of N,N-bis(3,4-dimethylphenyl)aminobenzene and 35.5 ml of DMF were placed, and 84.4 ml of phosphorus oxychloride was added dropwise thereto with stirring while cooling with ice water. After the addition was completed, the mixture solution was heated to 95° C. to carry out reaction for 5 hours. The reaction solution obtained was poured into 4 liters of warm water, followed by stirring for 1 hour. Thereafter, the precipitate was collected by filtration, and washed with a mixture of ethanol/water (1:1) to obtain 4-[N,N-bis(3,4-dimethylphenyl)amino]benzaldehyde in an amount of 107.6 g (yield: 79.0%).

Synthesis of 4-[N,N-bis(3,4-dimethylphenyl)-amino]styrene

Into a three-necked flask, 12.1 g of sodium hydride and 580 ml of 1,2-dimethoxyethane were placed, and 108.5 g of trimethylphosphonium bromide was added thereto with stirring at room temperature. Next, after a drop of absolute alcohol was added, the reaction was allowed to proceed at 70° C. for 4 hours. Then, 100.0 g of 4-[N,N-bis(3,4-dimethylphenyl)amino]benzaldehyde was added to the reaction mixture, to carry out reaction at 70° C. for 5 hours, followed by filtration to collect a cake. The cake was extracted with ether and the extract was put together with the filtrate and washed with water. Then, the ether solution was dehydrated with calcium chloride, and thereafter the ether was removed to obtain a crude product. After twice recrystallized from ethanol, acicular 4-[N,N-bis(3,4-dimethylphenyl)amino]styrene was obtained in an amount of 84.5 g (yield: 85.0%).

Hydrosilylation of 4-[N,N-bis(3,4-dimethyl-phenyl)amino]styrene

Into a three-necked flask, 40 ml of toluene, 6.0 g of triethoxysilane and 0.54 mmol of diplatinum (0) tris(tetramethyldivinyldisiloxane) in toluene were placed, and 20 ml of a toluene solution containing 9.9 g of 4-[N,N-bis(3,4-dimethylphenyl)amino]styrene was added dropwise with stirring at room temperature. After the addition was completed, the mixture was stirred at 70° C. for 3 hours, and thereafter the solvent was removed under reduced pressure to obtain oily pale yellow 4-[N,N-bis(3,4-dimethylphenyl)amino]-[2-(triethoxysilyl)ethyl]benzene in an amount of 13.4 g (yield: 90.1%).

Figure 2:
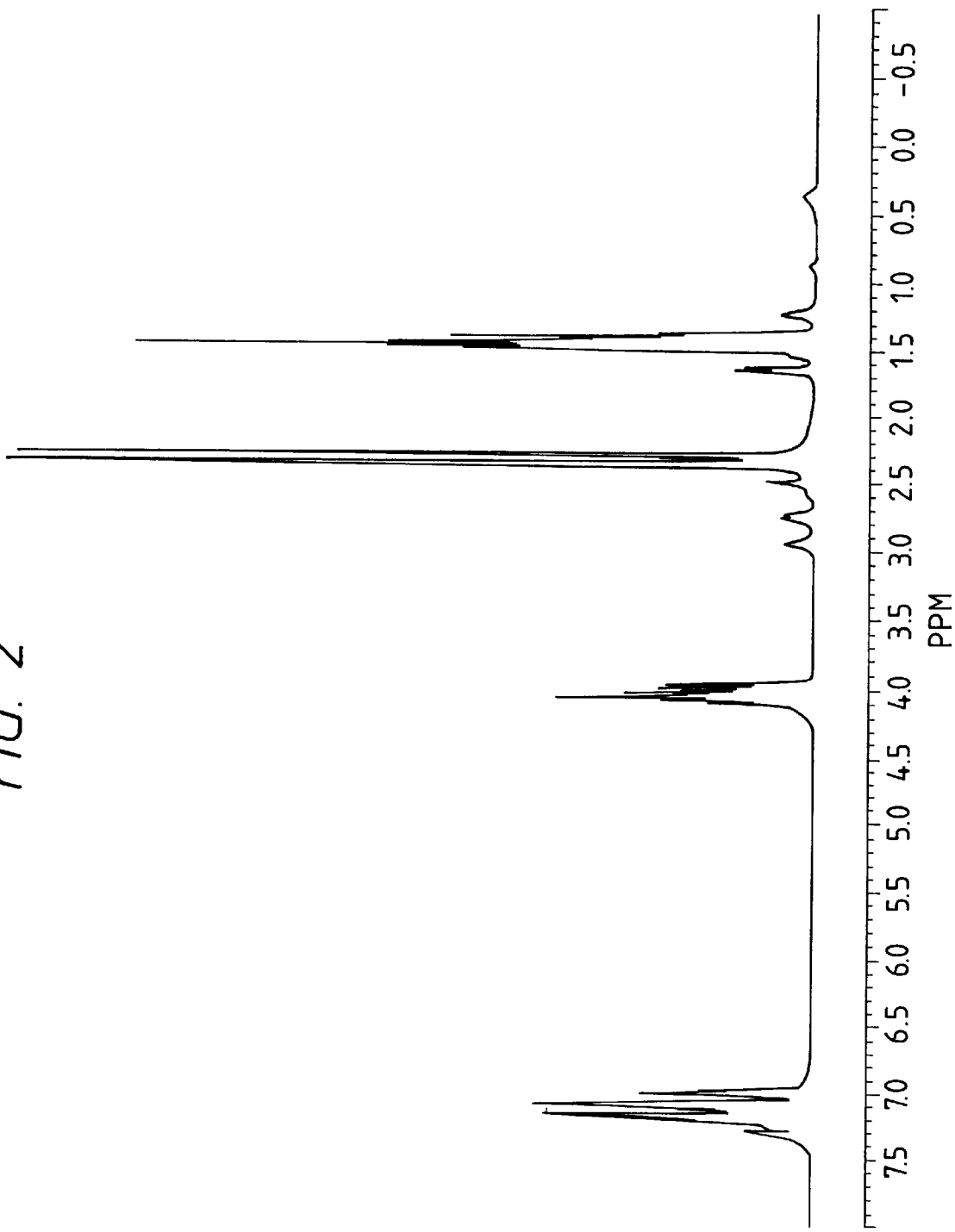
FIG. 2 shows an H-NMR spectrum of 4-[N,N-bis(3,4-dimethylphenyl)amino]-[2-(triethoxysilyl)ethyl]benzene in Example 4.
Figure 3:
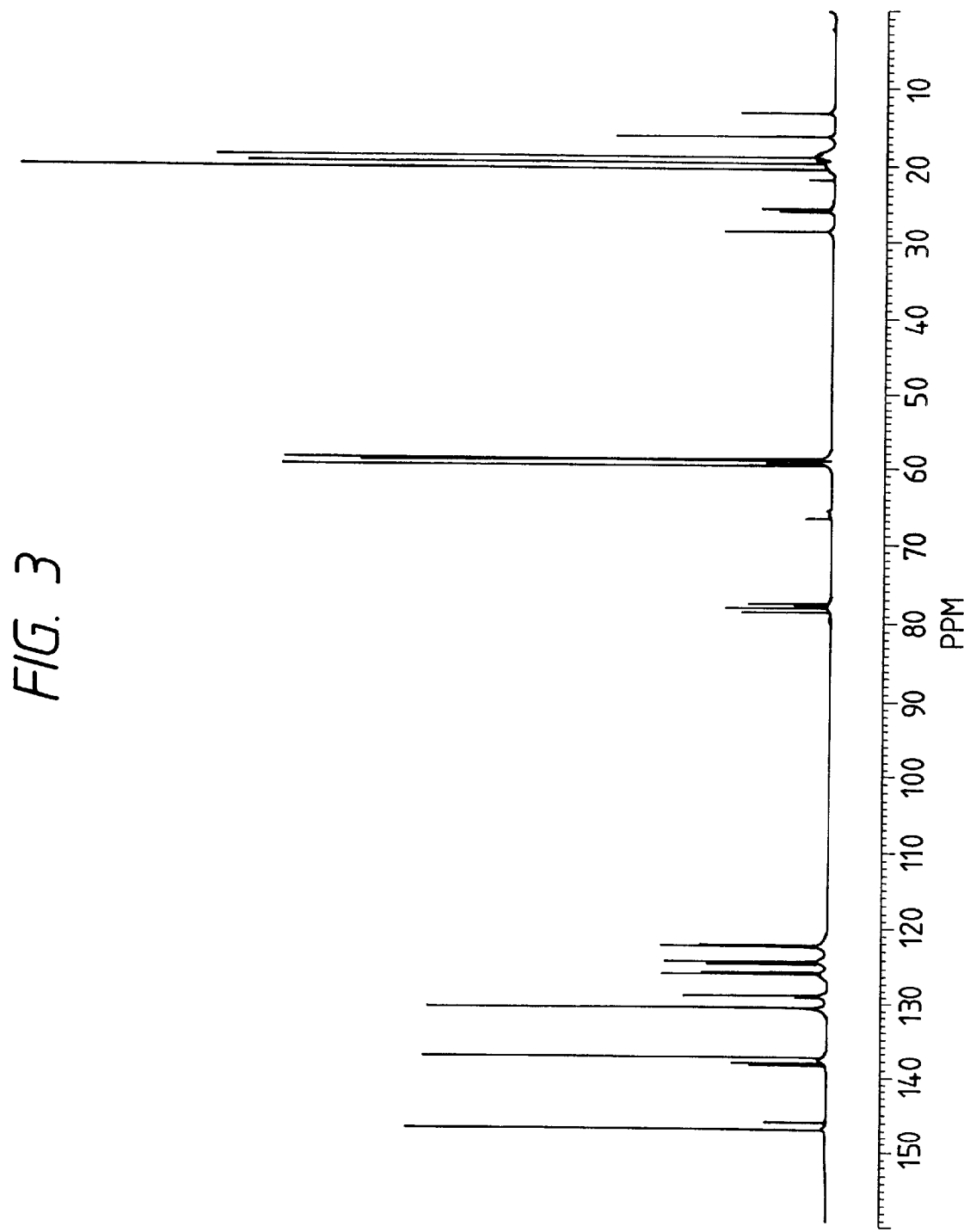
FIG. 3 shows a C-NMR spectrum of 4-[N,N-bis(3,4-dimethylphenyl)amino]-[2-(triethoxysilyl)ethyl]benzene in Example 4.

An H-NMR spectrum (measured by APC300, an NMR spectrometer manufactured by Bruker Co.) of the compound obtained is shown in FIG. 2. A C-NMR spectrum (measured by APC300, an NMR spectrometer manufactured by Bruker Co.) of the product compound is shown in FIG. 3.

Ionization potential of this compound measured by atmospheric photoelectron analysis (using a surface analyzer AC-1, manufactured by Riken Keiki K.K.) was 5.26 eV.

Example 5

Synthesis of 4-[N,N-bis(3,4-dimethylphenyl)amino]-[2-(triethoxysilyl)ethyl]benzene:

Hydrosilylation of 4-[N,N-bis(3,4-dimethyl-phenyl)amino]styrene

Into a three-necked flask, 40 ml of toluene, 6.0 g (37 mmol) of triethoxysilane and 0.34 mmol of platinum (II) dichloro(h-cycloocta-1,5-diene) were placed, and 20 ml of a toluene solution containing 9.9 g of 4-[N,N-bis(3,4-dimethylphenyl)amino]styrene was added dropwise with stirring at room temperature. After the addition was completed, the mixture was stirred at 70° C. for 3 hours, and thereafter the solvent was removed under reduced pressure to obtain oily pale yellow 4-[N,N-bis(3,4-dimethylphenyl)amino]-[2-(triethoxysilyl)ethylbenzene in an amount of 14.0 g (yield: 94.2%).

Ionization potential of this compound measured by atmospheric photoelectron analysis (using a surface analyzer AC-1, manufactured by Riken Keiki K.K.) was 5.31 eV.

Example 6

Synthesis of 4-[3-(triethoxysilyl)propyl]tri-phenylamine:

Synthesis of 4-bromotriphenylamine

Into a 200 ml three-necked flask, 8.0 g (45 mmol) of N-bromosuccinimide and 10.0 g (41 mmol) of triphenylamine were placed, followed by 150 ml of N,N-dimethylformamide. The mixture was stirred overnight at room temperature. Next, N,N-dimethylformamide was removed from the reaction, and the resulting solid matter was extracted with carbon tetrachloride. Then, carbon tetrachloride was removed, and the reaction product was recrystallized twice from ethanol to give a white solid, 4-bromotriphenylamine in an amount of 8.2 g (yield: 61.0%).

Synthesis of 4-N,N-diphenylaminoallylbenzene

Into a 300 ml four-necked flask, 1.0 g (40 mmol) of magnesium metal was placed, and the space air was replaced with nitrogen. Subsequently, 100 ml of diethyl ether was added and stirring was started. To the mixture being stirred, 30 ml of diethyl ether solution dissolving 8.6 g (27 mmol) of 4-bromotriphenylamine was slowly added dropwise. When about 3 ml of the 4-bromotriphenylamine solution was added dropwise, reflux slowly began. While being refluxed, the remaining 4-bromotriphenylamine solution was added dropwise. After the addition was completed, the reflux was further continued for 1 hour to obtain a Grignard reagent solution. The reagent solution thus obtained was cooled to room temperature, and then 40 ml of a diethyl ether solution containing 2.1 g (27 mmol) of allyl chloride was slowly added dropwise while cooling with ice. After the addition was completed, the reaction mixture was refluxed for 2 hours to age the reaction. Thereafter, 50 ml of water was added while cooling with ice, to effect hydrolysis. Next, the ether layer was collected, washed once with a saturated aqueous sodium hydrogencarbonate solution and washed twice with water, and then dried with anhydrous sodium sulfate. After drying, diethyl ether was removed to obtain a white solid, 4-N,N-diphenylaminoallylbenzene in an amount of 4.9 g (yield: 63.2%).

Hydrosilylation of 4-N,N-diphenylaminoallyl-benzene

Into a three-necked flask, 40 ml of toluene, 6.0 g (37 mmol) of triethoxysilane and 0.54 mmol of diplatinum (0) tris(tetramethyldivinyldisiloxane) in toluene were placed, and 20 ml of a toluene solution containing 9.7 g (34 mmol) of 4-N,N-diphenylaminoallylbenzene was added dropwise with stirring at room temperature. After the addition was completed, the mixture was stirred at 70° C. for 3 hours, and thereafter the solvent was removed under reduced pressure to obtain oily pale yellow 4-[3-(triethoxysilyl)propyl]triphenylamine in an amount of 10.7 g (yield: 70.1%).

Ionization potential of this compound measured by atmospheric photoelectron analysis (using a surface analyzer AC-1, manufactured by Riken Keiki K.K.) was 5.72 eV.

Example 7

Synthesis of 4-[4-(triethoxysilyl)butyl]tri-phenylamine:

Synthesis of 4-methyltriphenylamine

To 30 ml of o-dichlorobenzene, 4.5 g (27 mmol) of diphenylamine, 11.0 g (51 mmol) of p-iodotoluene, 5.5 g (40 mmol) of anhydrous sodium carbonate and 1.1 g of copper powder were added. The mixture was heated and refluxed with stirring for 7 hours. After the reaction was completed, the reaction solution was filtered. The filtrate was successively washed with an aqueous 35% sodium thiosulfate solution and saturated brine. The organic layer was dried with anhydrous sodium sulfate, and thereafter the solvent was removed. The resulting crude reaction product was recrystallized from ethanol to obtain 4-methyltriphenylamine in an amount of 5.7 g (yield: 81.4%).

Synthesis of 4-bromomethyltriphenylamine

Into a 300 ml three-necked flask, 6.9 g (39 mmol) of N-bromosuccinimide and 9.1 g (35 mmol) of 4-methyltriphenylamine were placed, and 100 ml of carbon tetrachloride was added thereto. Thereafter, the mixture was heated and refluxed overnight with stirring. After the reaction was completed, the reaction solution was cooled. Subsequently, the reaction was filtered, and the solvent was removed. The reaction product thus obtained was recrystallized from ethanol to obtain 4-bromomethyltriphenylamine in an amount of 10.8 g (yield: 91.2%).

Synthesis of 4-N,N-diphenylaminophenyl-1-butene

Into a 200 ml four-necked flask, 1.0 g (40 mmol) of magnesium metal was put, and the space air of the flask was replaced with nitrogen. Subsequently, 100 ml of diethyl ether was added and stirring was started. To the mixture, 20 ml of a diethyl ether solution in which 9.1 g (27 mmol) of 4-bromomethyltriphenylamine was dissolved was slowly added dropwise with stirring. When about 5 ml of the solution was added dropwise, reflux slowly started. While being refluxed, the remaining solution of 4-bromomethyltriphenylamine was added dropwise. After the addition was completed, the reflux was further continued for 1 hour to obtain a Grignard reagent solution. The reagent solution thus obtained was cooled to room temperature, and then 20 ml of a diethyl ether solution of 2.1 g (27 mmol) of allyl chloride was slowly added dropwise while cooling with ice. After the addition was completed, the reaction mixture was refluxed for 2 hours to age the reaction. Thereafter, 50 ml of water was added while cooling with ice, to effect hydrolysis. Next, the ether layer formed was collected, washed once with a saturated aqueous sodium hydrogencarbonate solution and twice with water, and then dried with anhydrous sodium sulfate. After drying, diethyl ether was removed to obtain a white solid, 4-N,N-diphenylaminophenyl-1-butene in an amount of 5.5 g (yield: 66.7%).

Hydrosilylation of 4-N,N-diphenylaminophenyl-1-butene

Into a three-necked flask, 40 ml of toluene, 9.9 g (60 mmol) of triethoxysilane and 0.018 mmol of diplatinum (0) tris(tetramethyldivinyldisiloxane) in toluene were placed, and 20 ml of a toluene solution containing 16.7 g (54.7 mmol) of 4-N,N-diphenylaminophenyl-1-butene was added dropwise with stirring at room temperature. After the addition was completed, the mixture was stirred at 70° C. for 3 hours, and thereafter the solvent was removed under reduced pressure to obtain oily pale yellow 4-[4-(triethoxysilyl) butyl]triphenylamine in an amount of 13.9 g (yield: 83.2%).

Ionization potential of this compound measured by atmospheric photoelectron analysis (using a surface analyzer AC-1, manufactured by Riken Keiki K.K.) was 5.69 eV.

Example 8

In the resin solution of Reference Example 1, 4-[2-(triethoxysilyl)ethyl]triphenylamine (Example 1) was added in an amount of 70% by weight based on the weight of the resin solid matter and mixed. The mixture was applied on a glass plate by means of a bar coater, followed by drying at 140° C. for 15 hours. Under microscopic observation, a uniform film had been formed.

Comparative Example 1

In the resin solution of Reference Example 1, triphenylamine was dissolved as a charge transporting compound in an amount of 30% by weight based on the weight of the resin, followed by mixing and curing in the same manner as in Example 8 to form a film. The film was cloudy, and microscopic observation confirmed deposition of triphenylamine.

Comparative Example 2

The procedure of Comparative Example 1 was repeated to form a film, except that the resin solution of Reference Example 2 was used. The film formed was less opaque, but microscopic observation confirmed deposition of crystals of triphenylamine.

Comparative Example 3

The procedure of Example 1 was repeated to obtain 4-[2-(trimethylsilyl)ethyl]triphenylamine, except that 6 g (60 mmol) of trimethylsilane was used in the hydrosilylation of the 4-vinyltriphenylamine obtained in Example 1. Using this, a film was formed in the same manner as in Comparative Example 1. As a result, the film was opaque, and separation of 4-[2-(trimethylsilyl)ethyl]triphenylamine was observed.

Example 9

Synthesis of 4-(N-ethyl-N-phenylamino)-[2-(triethoxysilyl) ethyl]benzene:

Synthesis of 4-(N-ethyl-N-phenylamino)-benzaldehyde

Into a three-necked flask, 82 g of diphenylethylamine and 35.5 ml of DMF were added, and 84.4 ml of phosphorus oxychloride was added dropwise thereto with stirring while cooling with ice water. After the addition was completed, the temperature was raised to 95° C. to carry out reaction for 5 hours. Thereafter, the resulting precipitate was collected by filtration, and washed with a mixture of ethanol/water (1:1) to obtain 4-(N-phenylamino)benzaldehyde in an amount of 62 g.

Synthesis of 4-(N-ethyl-N-phenylamino)styrene

Into a three-necked flask, 14.6 g of sodium hydride and 700 ml of 1,2-dimethoxyethane were placed, and 130.8 g of trimethylphosphonium bromide was added thereto with stirring at room temperature. Next, after a drop of absolute alcohol was added, the reaction was allowed to proceed at 70° C. for 5 hours. The reaction solution was filtered, and the filtrate and an ether-extract of the precipitate were put together, followed by washing with water. Then, the ether fraction was dehydrated with calcium chloride, and thereafter the ether was removed to obtain a crude reaction product. The reaction product was recrystallized from ethanol to obtain acicular pale yellow crystals in an amount of 62.4 g.

Hydrosilylation of 4-(N-ethyl-N-phenylamino)-styrene

Into a three-necked flask, 40 ml of toluene, 9.9 g (60 mmol) of triethoxysilane and 0.018 mmol of diplatinum (0) tris(tetramethyldivinyldisiloxane)in toluene were placed, and 20 ml of a toluene solution containing 7.6 g of 4-vinylphenyl(N-phenyl-N-ethyl)amine was added dropwise with stirring at room temperature. After the addition was completed, the mixture was stirred at 70° C. for 3 hours, and then the solvent was removed under reduced pressure to obtain oily pale yellow 4-(N-ethyl-N-phenylamino)-[2-(triethoxysilyl)ethyl]benzene in an amount of 7.8 g.

Ionization potential of this compound measured by atmospheric photoelectron analysis (using a surface analyzer AC-1, manufactured by Riken Keiki K.K.) was 6.3 eV.

Example 10

A curable composition was prepared by adding to 100 parts by weight of the curable resin solution of Reference Example 1, 200 parts by weight of toluene and 40 parts by weight of the 4-(N-ethyl-N-phenylamino)-[2-(triethoxysilyl)ethyl] benzene synthesized in Example 9. On an Al base sheet of 50 μm thick, the composition was applied by dip coating. The coating formed was dried and heat-cured at 140° C. for 4 hours to form a surface protective film of 2 μm thick.

The sheet thus obtained was set on a Taber's abrasion resistance tester (manufactured by Yasuda Seiki K.K.; 500 g load×2; wrapping tape #2000, available from Fuji Photo Film Co., Ltd.; 1,000 r.p.m.) to measure the depth of wear. As a result, it was as good as 0.8 μm or less.

The Al base sheet was grounded and electrostatically charged to 700 V by a corona charging assembly. The residual potential after 5 seconds was measured to find that it was 350 V or below.

Example 11

A curable composition was prepared by adding to 100 parts by weight of the curable resin solution of Reference Example 1, 200 parts by weight of toluene and 40 parts by weight of the 4-(N, N-bis( 3,4-dimethylphenyl)amino]-[2-(triethoxysilyl)ethyl] benzene synthesized in Example 4. On an Al base sheet of 50 μm thick, the composition was applied by dip coating. The coating formed was dried and heat-cured at 140° C. for 4 hours to form a surface protective film of 2 μm thick.

The sheet thus obtained was set on a Taber's abrasion resistance tester (manufactured by Yasuda Seiki K.K.; 500 g load×2; wrapping tape #2000, available from Fuji Photo Film Co., Ltd.; 1,000 r.p.m.) to measure the depth of wear. As a result, it was as good as 0.5 μm or less.

The Al base sheet was also grounded and electrostatically charged to 700 V by a corona charging assembly. The residual potential after 5 seconds was measured to find that it was 50 V or below, showing good charge elimination.

Comparative Example 4

On an Al sheet of 50 μm thick, a composition prepared by dissolving 5 parts by weight of polycarbonate resin (trade name: Z-200; available from Mitsubishi Gas Chemical Company, Ltd.) in 100 parts by weight of chlorobenzene was applied by dip coating. The coating formed was dried at 120° C. for 1 hour to form a protective film of 5 μm thick.

The sheet thus obtained was set on a Taber's abrasion resistance tester (manufactured by Yasuda Seiki K.K.; 500 g load×2; wrapping tape #2000; 1,000 r.p.m.) to measure the depth of wear. As a result, it was as bad as 4 μm or more.

The Al base sheet was also grounded and electrostatically charged to 700 V by a corona charging assembly. The residual potential after 5 seconds was measured to find that it was 500 V or above, showing insufficient charge elimination.

Comparative Example 5

On an Al base sheet of 50 μm thick, a curable composition prepared by adding 200 parts by weight of toluene to 100 parts by weight of the curable resin solution of Reference Example 1 was applied by dip coating. The coating formed was dried and heat-cured at 140° C. for 4 hours to form a 2 μm thick, surface protective film.

The sheet thus obtained was set on a Taber's abrasion resistance tester (manufactured by Yasuda Seiki K.K.; 500 g load×2; wrapping tape #2000; 1,000 r.p.m.) to measure the depth of wear. As a result, it was as good as 0.5 μm or less.

The Al base sheet was also grounded and electrostatically charged to 700 V by a corona charging assembly. The residual potential after 5 seconds was measured to find that it was 450 V, showing insufficient charge elimination, however.

Example 12

On an Al sheet of 50 μm thick, a composition prepared by dissolving 20 parts by weight of polycarbonate resin (trade name: Z-200; available from Mitsubishi Gas Chemical Company, Ltd.) in 100 parts by weight of chlorobenzene was applied by dip coating. The coating formed was dried at 120° C. for 1 hour to form a film of 50 μm thick.

Next, on the above sheet coated with polycarbonate resin, a curable composition prepared by adding and dissolving in 100 parts by weight of toluene 55 parts by weight of the organosilicon-modified triarylamine compound synthesized in Example 5 and 100 parts by weight of the curable resin of Reference Example 3 was applied by spray coating. The coating formed was dried and heat-cured at 120° C. for 5 hours to form a protective film with a layer thickness of 3 μm.

The protective film had a pencil hardness of 5H and a contact angle with water of 105°, and it was readily cleaned even when immersed in water or mineral oil.

The sheet thus obtained was set on a Taber's abrasion resistance tester (manufactured by Yasuda Seiki K.K.; 500 g load×2; wrapping tape #2000; 1,000 r.p.m.) to measure the depth of wear. As a result, it was as good as 0.5 μm or less.

Comparative Example 6

On a stainless steel sheet of 1 mm thick, a solution prepared by dissolving in 70 parts by weight of chlorobenzene 5 parts by weight of a triarylamine compound having the following structure and 5 parts by weight of polycarbonate resin (trade name: Z-200; available from Mitsubishi Gas Chemical Company, Ltd.) was applied by dip coating so as to provide a layer thickness of 10 μm after drying at 120° C. for 1 hour. The film finally formed had a contact angle with water of as small as 75°, and hence, contaminants were not readily removed.

This sheet was set on a Taber's abrasion resistance tester (manufactured by Yasuda Seiki K.K.; 500 g load×2; wrapping tape #2000, available from Fuji Photo Film Co., Ltd.; 1,000 r.p.m.) to measure the depth of wear. As a result, it was as large as 5 μm.

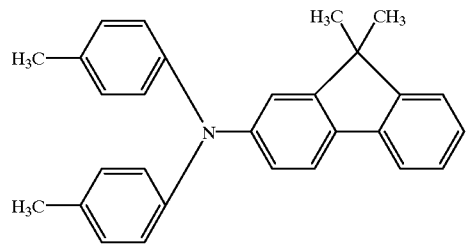

What is claimed is:
1. An organosilicon-modified charge transporting compound having a structure represented by the following

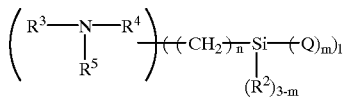

Q represents a hydrolytic group or a hydroxyl group, $R^2$ represents a monovalent hydrocarbon group or a halogen-substituted monovalent hydrocarbon group having 1 to 15 carbon atoms, n is 1 to 18, m is 1 to 3, P is 1 to 5, $R^3$, $R^4$ and $R^5$ each represent an organic group, at least one of which represents an aromatic hydrocarbon ring group or a heterocyclic group and $R^3$, $R^4$ and $R^5$ are the same or different.

2. The organosilicon-modified charge transporting compound according to claim 1, wherein said hydrolytic group is a group represented by —$OR^1$, where $R^1$ represents an alkyl or alkoxyalkyl group having 1 to 6 carbon atoms.

3. The organosilicon-modified charge transporting compound according to claim 1, which has an ionization potential of from 4.5 eV to 6.2 eV.

4. The organosilicon-modified charge transporting compound according to claim 1, wherein said charge transporting group has a structure represented by the following Formula (II).

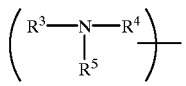 (II)

wherein $R^3$, $R^4$ and $R^5$ each represent an organic group, at least one of which represents an aromatic hydrocarbon ring group or a heterocyclic group, and $R^3$, $R^4$ and $R^5$ may be the same or different.

5. A curable composition having a charge transporting ability, which comprises;
   a cure type resin chiefly composed of an organosilicon high polymer in which monovalent hydrocarbon groups bonded to silicon atoms and the silicon atoms are in a ratio of from 0.5 to 1.5; and
   an organosilicon-modified charge transporting compound having a structure represented by the following

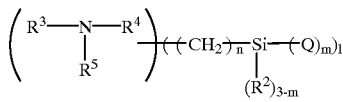

Q represents a hydrolytic group or a hydroxyl group, $R^2$ represents a monovalent hydrocarbon group or a halogen-substituted monovalent hydrocarbon group having 1 to 15 carbon atoms, n is 1 to 18, m is 1 to 3, l is 1 to 5, $R^3$, $R^4$ and $R^5$ each represent an group, at least one of which represents an aromatic hydrocarbon ring group or a heterocyclic group and $R^3$, $R^4$ and $R^5$ are the same or different.

6. The curable composition according to claim 5, wherein said hydrolytic group is a group represented by —$OR^1$, where $R^1$ represents an alkyl or alkoxyalkyl group having 1 to 6 carbon atoms.

7. The curable composition according to claim 5, wherein said organosilicon high polymer is an organopolysiloxane having a structural unit represented by the following Formula (III):

$$R^6{}_n SiO_{(4-n-m)/2}(OR^7)_m \quad (III)$$

wherein $R^6$ represents a straight-chain or branched alkyl group or alkenyl group having 1 to 18 carbon atoms, or an aryl group; $R^7$ represents an alkyl group having 1 to 4 carbon atoms; n is 0.5 to 1.5 on the average; and m is 0.01 to 1.5 on average.

8. The curable composition according to claim 5, wherein said organosilicon-modified charge transporting compound is contained in an amount of from 20 parts by weight to 200 parts by weight based on 100 parts by weight of the organosilicon high polymer of the cure type resin.

9. The curable composition according to claim 5, wherein said charge transporting group has a structure represented by the following Formula (II):

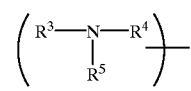 (II)

wherein $R^3$, $R^4$ and $R^5$ each represent an organic group, at least one of which represents an aromatic hydrocarbon ring group or a heterocyclic group, and $R^3$, $R^4$ and $R^5$ may be the same or different.

10. The curable composition according to claim 5, wherein said cure type resin contains a silane compound represented by the following Formula (IV):

$$R^8{}_a SiX_{4-a} \quad (IV)$$

wherein $R^8$ represents a straight-chain or branched alkyl or alkenyl group having 1 to 18 carbon atoms, or a phenyl group; X represents a hydrolytic group; and a represents a molar ratio.

* * * * *

UNITED STATES PATENT AND TRADEMARK OFFICE
CERTIFICATE OF CORRECTION

PATENT NO. : 6,376,695 B1
DATED : April 23, 2002
INVENTOR(S) : Nobuo Kushibiki et al.

It is certified that error appears in the above-identified patent and that said Letters Patent is hereby corrected as shown below:

Column 1,
Line 49, "small" should read -- low --.

Column 2,
Line 5, "small" should read -- low --; and
Line 25, "comprises;" should read -- comprises: --.

Column 3,
Line 14, "When," should read -- When --.

Column 7,

Line 6, 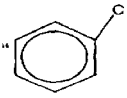

Column 22,

Line 62, 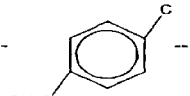

Column 28,
Line 31, "O-Dichrolobenzine" should read -- O-Dichlorobenzene --.

Column 42,
Line 7, "to" should be deleted;
Line 8, "what" should read -- what is --.

Column 43,
Line 19, "group," (first occurrence) should read -- groups, --; and
Line 61, "before hand," should read -- beforehand, --.

Column 44,
Line 47, "20 molt" should read -- 20 mol% --.

Column 46,
Line 16, "5 liter" should read -- 5 liters --.

UNITED STATES PATENT AND TRADEMARK OFFICE
CERTIFICATE OF CORRECTION

PATENT NO. : 6,376,695 B1
DATED : April 23, 2002
INVENTOR(S) : Nobuo Kushibiki et al.

It is certified that error appears in the above-identified patent and that said Letters Patent is hereby corrected as shown below:

Column 47,
Line 63, "ethylbenzine" should read -- ethyl]benzene --.

Column 53,
Line 10, "P" should read -- 1 --; and
Lines 21-35, Claim 4 should be deleted.

Column 54,
Line 2, "group," should read -- organic group, --; and
Lines 27-40, Claim 9 should be deleted.

Signed and Sealed this

Seventeenth Day of August, 2004

JON W. DUDAS
*Acting Director of the United States Patent and Trademark Office*